US011427876B2

(12) United States Patent
de Vlaminck et al.

(10) Patent No.: US 11,427,876 B2
(45) Date of Patent: *Aug. 30, 2022

(54) CELL-FREE NUCLEIC ACIDS FOR THE ANALYSIS OF THE HUMAN MICROBIOME AND COMPONENTS THEREOF

(71) Applicant: The Board of Trustees of the Leland Stanford Junior University, Stanford, CA (US)

(72) Inventors: Iwijn de Vlaminck, Stanford, CA (US); Michael Kertesz, Menlo Park, CA (US); Kiran Kaur Khush, Stanford, CA (US); Mark Alec Kowarsky, Kowarsky (AU); Lance Martin, Half Moon Bay, CA (US); Stephen R. Quake, Stanford, CA (US); Hannah Valantine, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/347,247

(22) Filed: Jun. 14, 2021

(65) Prior Publication Data

US 2021/0301356 A1    Sep. 30, 2021

Related U.S. Application Data

(63) Continuation of application No. 16/554,286, filed on Aug. 28, 2019, which is a continuation of application No. 14/536,300, filed on Nov. 7, 2014, now Pat. No. 10,450,620.

(60) Provisional application No. 61/901,114, filed on Nov. 7, 2013, provisional application No. 61/901,857, filed on Nov. 8, 2013.

(51) Int. Cl.
| | |
|---|---|
| *G16B 30/00* | (2019.01) |
| *G16B 20/00* | (2019.01) |
| *G16B 30/10* | (2019.01) |
| *G16B 20/20* | (2019.01) |
| *C12Q 1/70* | (2006.01) |
| *C12Q 1/6883* | (2018.01) |
| *C12Q 1/689* | (2018.01) |
| *C12Q 1/6895* | (2018.01) |

(52) U.S. Cl.
CPC ............ *C12Q 1/705* (2013.01); *C12Q 1/689* (2013.01); *C12Q 1/6883* (2013.01); *C12Q 1/6895* (2013.01); *C12Q 1/701* (2013.01); *G16B 20/00* (2019.02); *G16B 20/20* (2019.02); *G16B 30/00* (2019.02); *G16B 30/10* (2019.02)

(58) Field of Classification Search
None
See application file for complete search history.

(56) References Cited

U.S. PATENT DOCUMENTS

| | | |
|---|---|---|
| 6,258,540 B1 | 7/2001 | Lo et al. |
| 6,753,137 B2 | 6/2004 | Lo et al. |
| 6,977,162 B2 | 12/2005 | Dhallan |
| 7,208,274 B2 | 4/2007 | Dhallan |
| RE39,920 E | 11/2007 | Umansk et al. |
| 7,332,277 B2 | 2/2008 | Dhallan |
| 7,442,506 B2 | 10/2008 | Dhallan |
| 7,598,060 B2 | 10/2009 | Dhallan |
| 7,718,370 B2 | 5/2010 | Dhallan |
| 7,727,720 B2 | 6/2010 | Dhallan |
| 7,803,929 B2 | 9/2010 | Melkonyan et al. |
| 7,914,982 B2 | 3/2011 | Melkonyan et al. |
| 7,973,154 B2 | 7/2011 | Melkonyan et al. |
| 8,682,592 B2 | 3/2014 | Rabinowitz et al. |
| 8,703,652 B2 | 4/2014 | Quake et al. |
| 10,450,620 B2 | 10/2019 | de Vlaminck et al. |
| 10,450,650 B2 | 10/2019 | Sultana et al. |
| 2002/0015955 A1 | 2/2002 | Meyerson et al. |
| 2004/0209299 A1 | 10/2004 | Pinter et al. |
| 2005/0202414 A1 | 9/2005 | Jia et al. |
| 2010/0068711 A1 | 3/2010 | Umansky et al. |
| 2012/0021412 A1 | 1/2012 | Melkonyan et al. |
| 2012/0077185 A1 | 3/2012 | Oliphant et al. |
| 2012/0190663 A1 | 7/2012 | Gornik et al. |
| 2012/0231446 A1 | 9/2012 | Heckel et al. |

(Continued)

FOREIGN PATENT DOCUMENTS

| | | |
|---|---|---|
| EP | 1856295 A2 | 11/2007 |
| EP | 1885877 A2 | 2/2008 |

(Continued)

OTHER PUBLICATIONS

Huttunen et al. Fatal Outcome in Bacteremia is Characterized by High Plasma Cell Free DNA Concentration and Apoptotic DNA Fragmentation: A Prospective Cohort Study, . PLoS One 6(7): e21700. doi: 10.1371/journal.pone.0021700.*

Jeng et al. Application of a 16S rRNA PCR-High-Resolution Melt Analysis Assay for Rapid Detection of Salmonella Bacteremia, Published ahead of print Dec. 28, 2011, Journal of Clinical Microbiology p. 1122-1124.*

Won et al. Rapid Identification of Bacterial Pathogens in Positive Blood Culture Bottles by Use of a Broad-Based PCR Assay Coupled with High-Resolution Melt Analysis, Journal of Clinical Microbiology, Sep. 2010, p. 3410-3413 vol. 48, No. 9 0095-1137/10/$12.00 doi:10.1128/JCM.00718-10.*

(Continued)

*Primary Examiner* — Joseph Woitach
(74) *Attorney, Agent, or Firm* — Pamela J. Sherwood; Bozicevic, Field & Francis LLP

(57) ABSTRACT

Methods, devices, compositions and kits are provided for analysis of the microbiome or individual components thereof in an individual. The methods find use in a determination of infection, in analysis of the microbiome structure, in determining the immunocompetence of an individual, and the like. In some embodiments of the invention, the individual is treated with an therapeutic regimen, e.g. drugs, diet, radiation therapy, and the like.

29 Claims, 11 Drawing Sheets

(56) References Cited

U.S. PATENT DOCUMENTS

| | | |
|---|---|---|
| 2012/0295810 A1 | 11/2012 | Quake et al. |
| 2013/0024127 A1 | 1/2013 | Stuelpnagel et al. |
| 2013/0178544 A1 | 7/2013 | Melkonyan et al. |
| 2013/0237431 A1 | 9/2013 | Lo et al. |
| 2013/0245961 A1 | 9/2013 | Lo et al. |
| 2013/0252835 A1 | 9/2013 | Koh et al. |
| 2014/0066317 A1 | 3/2014 | Talasaz et al. |
| 2014/0147851 A1 | 5/2014 | Qian et al. |
| 2014/0242582 A1 | 8/2014 | Oliphant et al. |
| 2014/0274740 A1 | 9/2014 | Srinivasan et al. |
| 2015/0133391 A1 | 5/2015 | de Vlaminic et al. |
| 2016/0017420 A1 | 1/2016 | Koh et al. |
| 2016/0304953 A1 | 10/2016 | Chen et al. |
| 2017/0145507 A1 | 5/2017 | Koh et al. |
| 2017/0145508 A1 | 5/2017 | Koh et al. |
| 2017/0145509 A1 | 5/2017 | Koh et al. |

FOREIGN PATENT DOCUMENTS

| | | | |
|---|---|---|---|
| EP | 2351857 A1 | 8/2011 | |
| JP | 2013509883 | 3/2013 | |
| JP | 2013511269 | 4/2013 | |
| WO | WO-2011057061 A1 | 5/2011 | |
| WO | WO2012159023 | 11/2012 | |
| WO | WO 2012168815 | 12/2012 | |
| WO | WO2013052907 A2 | 4/2013 | |
| WO | WO2013132305 A1 | 9/2013 | |
| WO | WO 2013156627 | 10/2013 | |
| WO | WO 2013159035 | 10/2013 | |
| WO | WO2013188846 A1 | 12/2013 | |
| WO | WO2014039556 A1 | 3/2014 | |
| WO | WO2014068075 A1 | 5/2014 | |
| WO | WO2014149134 A2 | 9/2014 | |
| WO | 20155070086 A1 | 5/2015 | |

OTHER PUBLICATIONS

Wang et al. (2012) "The Complex Exogenous RNA Spectra in Human Plasma: An Interface with Human Gut Biota?" PloS one 7:12 e51009 13 pages.

Anderson, et al. Clonal sequences recovered from plasma from patients with residual HIV-1 viremia and on intensified antiretroviral therapy are identical to replicating viral RNAs recovered from circulating resting CD4+ T cells. J Virol. May 2011;85(10):5220-5223. doi: 10.1128/JVI.00284-11. Epub Mar. 2, 2011.

Arbabi et al. (2016) "Cell-free DNA fragment-size distribution analysis for non-invasive prenatal CNV prediction" 32;11, pp. 1662-1669.

Ausubel et al., "Current Protocols in Molecular Biology", Dec. 4, 2003, pp. 1-4648, John Wiley & Sons Inc., Hoboken, NJ.

Barzon, et al. Applications of next-generation sequencing technologies to diagnostic virology. Int J Mol Sci. 2011;12(11):7861-7884. doi: 10.3390/ijms12117861. Epub Nov. 14, 2011.

Beck et al. "Profile of the circulating DNA in apparently healthy individuals". Clin Chem. Apr. 2009;55(4):730-8. doi: 10.1373/clinchem.2008.113597. Epub Jan. 30, 2009.

Beck, et al. "Digital droplet PCR for rapid quantification of donor DNA in the circulation of transplant recipients as a potential universal biomarker of graft injury". Clin Chem. Dec. 2013;59(12):1732-1741. doi: 10.1373/clinchem.2013.210328. Epub Sep. 23, 2013.

Best "Viral Subversion of Apoptotic Enzymes: Escape from Death Row". Annu Rev Microbiol. 2008; 62: 171-192. Author manuscript; available in PMC Oct. 7, 2008.

Burnham et al. (2016) "Single-stranded DNA library preparation uncovers the origin and diversity of ultrashort cell-free DNA in plasma" 6:27859 | DOI: 10.1038/srep27859.

Cotten, et al. "Full-genome deep sequencing and phylogenetic analysis of novel human betacoronavirus". Emerg Infect Dis. May 2013;19(5):736-742B. doi: 10.3201/eid1905.130057.

Dhallan, et al. "A non-invasive test for prenatal diagnosis based on fetal DNA present in maternal blood: a preliminary study". Lancet. Feb. 10, 2007;369(9560):474-481. doi: 10.1016/S0140-6736(07)60115-9.

Donaldson, et al. "Metagenomic analysis of the viromes of three North American bat species: viral diversity among different bat species that share a common habitat". J Virol. Dec. 2010;84(24):13004-13018. doi: 10.1128/JVI.01255-10. Epub Oct. 6, 2010.

Drosten, et al. "Identification of a novel coronavirus in patients with severe acute respiratory syndrome". N Engl J Med. May 15, 2003;348(20):1967-1976. doi: 10.1056/NEJMoa030747. Epub Apr. 10, 2003.

EP14860535.5 Extended European Search Report dated Apr. 25, 2017.

Ercolini, "High-Throughput Sequencing and Metagenomics: Moving Forward in the Culture-Independent Analysis of Food Microbial Ecology", Applied and Environmental Microbiology, May 2013, pp. 3148-3155, vol. 79, No. 10, American Society for Microbiology, Washington, D.C.

Fan et al., "Noninvasive diagnosis of fetal aneuploidy by shotgun sequencing DNA from maternal blood", PNAS, Oct. 21, 2008, pp. 16266-16271, vol. 105, No. 42, National Academy of Sciences, Washington, D.C.

Freshney et al., "Animal Cell Culture: A Practical Approach", Jan. 1986, p. 53, Oxford University Press, Oxford, United Kingdom.

Gal et al., "Detection of Plasmodium falciparum DNA in Plasma", Ann. N.Y. Acad. Sci., Sep. 2001, pp. 234-238, vol. 945, Issue 1, Wiley, Hoboken, NJ.

Grumaz et al. "Next-generation sequencing diagnostics of bacteremia in septic patients". Genome Medicine, 2016, 8:73.

Highlander "High throughput sequencing methods for microbiome profiling: application to food animal systems", Animal Health Research Reviews, Jun. 2012, vol. 13(1); pp. 40-53.

Horlitz et al., "Yields of Viral and Circulating Cell-Free Nucleic Acids Using the QIAamp Circulating Nucleic Acid Kit", 2010, In: Gahan P. (eds) Circulating Nucleic Acids in Plasma and Serum. pp. 259-268, Springer, Berlin, Germany.

Houldcroft, et al. Clinical and biological insights from viral genome sequencing. Nat Rev Microbiol. Mar. 2017;15(3):183-192. doi: 10.1038/nrmicro.2016.182. Epub Jan. 16, 2017.

Hui, D.S. "Tracking the transmission and evolution of MERS-CoV." Lancet. Dec. 14, 2013;382(9909):1962-1964. doi: 10.1016/S0140-6736(13)61955-8. Epub Sep. 20, 2013.

Hui, et al. "SARS: clinical features and diagnosis". Respirology. Nov. 2003;8 Suppl(Suppl 1):S20-S24. doi: 10.1046/j.1440-1843.2003.00520.x.

Kato-Hayashi et al., "Use of Cell-Free Circulating Schistosome DNA in Serum, Urine, Semen, and Saliva To Monitor a Case of Refractory Imported Schistosomiasis Hematobia", Jul. 24, 2013, J. Clin. Micro., pp. 3435-3438, vol. 51, No. 10, American Society for Microbiology, Washington DC.

Kuroda, et al. "Characterization of quasispecies of pandemic 2009 influenza A virus (A/H1N1/2009) by de novo sequencing using a next-generation DNA sequencer". PLoS One. Apr. 23, 2010;5(4):e10256. doi: 10.1371/journal.pone.0010256.

Law et al., "Identification of Hepatotropic Viruses from Plasma Using Deep Sequencing: A Next Generation Diagnostic Tool", Apr. 2013, pp. 1-13, vol. 8, Issue 4, e60595, PLOS One, San Francisco, CA.

Li et al., "Detection and identification of plasma bacterial and viral elements in HIV/AIDS patients in comparison to healthy adults", Clinical Microbiology and Infection, Nov. 2012, pp. 1126-1133, vol. 18, Issue 11, John Wiley & Sons, Inc., Hoboken, NJ.

Moreira et al., "Usefulness of cell-free plasma DNA, procalcitonin and C-reactive protein as markers of infection in febrile patients", Annals of Clinical Biochemistry, Apr. 26, 2010, pp. 253-258, 47, Association for Clinical Biochemistry and Laboratory Medicine, London, England.

Ng, et al. "Quantitative analysis and prognostic implication of SARS coronavirus RNA in the plasma and serum of patients with severe acute respiratory syndrome". Clin Chem. Dec. 2003;49(12):1976-1980. doi: 10.1373/clinchem.2003.024125.

(56) References Cited

OTHER PUBLICATIONS

Ng, et al. "Serial analysis of the plasma concentration of SARS coronavirus RNA in pediatric patients with severe acute respiratory syndrome". Clin Chem. Dec. 2003;49(12):2085-2088. doi: 10.1373/clinchem.2003.024588.

Nikkari, et al. (2001) "Does blood of healthy subjects contain bacterial ribosomal DNA?", Journal clinical microbiology, vol. 39, No. 5, May 2001. p. 1956-1959.

Notice of Allowance dated Aug. 7, 2019 for U.S. Appl. No. 14/536,300.

O'Brien "Viruses and apoptosis". J Gen Virol. Aug. 1998;79 ( Pt 8):1833-45.

Office action dated Jul. 27, 2018 for U.S. Appl. No. 14/536,300.

Office action dated Oct. 4, 2017 for U.S. Appl. No. 14/536,300.

Palacios, et al. "A new arenavirus in a cluster of fatal transplant-associated diseases". N Engl J Med. Mar. 6, 2008;358(10):991-998. doi: 10.1056/NEJMoa073785. Epub Feb. 6, 2008.

Quan, et al. "Identification of a Severe Acute Respiratory Syndrome CoronavirLike Virus in a Leaf-Nosed Bat in Nigeria". mBio. Oct. 12, 2010. 1(4):e00208-10. DOI: 10.1128/mBio.00208-10.

Rhodes et al., "Plasma DNA concentration as a predictor of mortality and sepsis in critically ill patients", Crit. Care, Apr. 13, 2006, pp. 1-7, vol. 10, No. 2, BioMed Central Ltd., London, United Kingdom.

Sambrook et al., "Culinary Biology", Molecular Cloning: A Laboratory Manual, Apr. 6, 1990, pp. 17-18,vol. 61, Cell Press, Cambridge, MA.

Saukkonen, et al. "Cell-free plasma DNA as a predictor of outcome in severe sepsis and septic shock". Clin Chem. Jun. 2008;54(6):1000-7. doi: 10.1373/clinchem.2007.101030. Epub Apr. 17, 2008.

Semenov et al., "Unbiased approach to profile the variety of small non-coding RNA of human blood plasma with massively parallel sequencing technology", Expert Opinion on Biological Therapy, Apr. 18, 2012, pp. S43-S51, vol. 12, Informa UK Limited, London, United Kingdom.

Sharma et al., "Mass spectrometric based analysis, characterization and applications of circulating cell free DNA isolated from human body fluids", Int J Mass Spectrom., Jul. 1, 2011, pp. 172-183, vol. 304, Issues 2-3, Elsevier, New York City, NY.

Supplement Information on Li et al. Detection and identification of plasma bacterial and viral elements in HIV/AIDS patients in comparison to healthy adults. Clin Microbiol Infect. Nov. 2012;18(11):1126-33.

Swinkels et al., "Effects of Blood-Processing Protocols on Cell-free DNA Quantification in Plasma", Clin. Chem., Mar. 2003, pp. 525-526, vol. 49, Issue 3, American Association for Clinical Chemistry, Washington, D.C.

Vernon et al., "Analysis of 16S rRNA gene sequences and circulating cell-free DNA from plasma of chronic fatigue syndrome and non-fatigued subjects", BMC Microbiology, Dec. 23, 2002, pp. 1-6, BioMed Central Ltd., London, United Kingdom.

Wang et al. "The complex exogenous RNA spectra in human plasma: an interface with human gut biota?" PLoS One. 2012;7(12):e51009.

Wang, et al. Detection of Severe Acute Respiratory Syndrome Coronavirus RNA in Plasma during the Course of Infection. J Clin Microbiol. Feb. 2005; 43(2): 962-965. doi: 10.1128/JCM.43.2.962-965.2005.

Wichmann et al., "Diagnosing Schistosomiasis by Detection of Cell-Free Parasite DNA in Human Plasma", PLoS Neg. Trop. Dis., Apr. 21, 2009, pp. 1-9, vol. 3, Issue 4, e422, PLoS, San Francisco, CA.

Yuan et al. "Modulation of Apoptotic Pathways by Human Papillomaviruses (HPV): Mechanisms and Implications for Therapy". Viruses. Dec. 2012; 4(12): 3831-3850.

Zhao, et al. "Moderate mutation rate in the SARS coronavirus genome and its implications". BMC Evol Biol. Jun. 28, 2004;4:21. doi: 10.1186/1471-2148-4-21.

Chen et al., (2012) "Total serum DNA and DNA integrity: diagnostic value in patients with hepatitis B virus-related hepatocellular carcinoma" Pathology, vol. 44, No. 4, pp. 318-324.

Kowarsky et al., (2017) "Numerous uncharacterized and highly divergent microbes which colonize humans are revealed by circulating cell-free DNA" PNAS, vol. 114, No. 36, pp. 9623-9628.

Stephan et al., (2001) "Blood and alveolar lymphocyte subsets in pulmonary cytomegalovirus infection after lung transplantation", BMC Infectious Diseases, vol. 1, No. 15, pp. 1-7.

Brecher et al., (2005) "Bacterial Contamination of Blood Components" Clinical Microbiology Reviews, 18:195-204.

\* cited by examiner

CELL-FREE NUCLEIC ACIDS FOR THE ANALYSIS OF THE HUMAN MICROBIOME AND COMPONENTS THEREOF

CROSS REFERENCE

This application claims benefit and is a Continuation of application Ser. No. 16/554,286, filed Aug. 28, 2019, which claims benefit of application Ser. No. 14/536,300 filed Nov. 7, 2014, which claims benefit of U.S. Provisional Patent Application No. 61/901,114 filed Nov. 7, 2013, and U.S. Provisional Patent Application No. 61/901,857, filed Nov. 8, 2013, which applications are incorporated herein by reference in their entirety.

GOVERNMENT RIGHTS

This invention was made with Government support under grant RC4AI092673 awarded by the National Institutes of Health. The Government has certain rights in this invention.

BACKGROUND OF THE INVENTION

The human microbiome is now recognized as an important component of human health. Community level analyses have shed light on factors that shape the structure of the bacterial and viral components of the microbiome, such as age, diet, geographical location, antibiotic treatment and disease. For example, an individual microbiome can be altered by infection with a pathogenic organism, such that there is an increased prevalence of that organism systemically, or in an undesirable tissue. The microbiome can also be altered by changes in the immunocompetence of the individual.

For a variety of purposes it would be desirable to have a method for rapid identification of specific microbiome components, e.g. the presence and prevalence of commensal, mutualistic, parasitic, opportunistic and pathogenic organisms in an individual microbiome; as well as an analysis of the overall microbiome structure. The present invention provides sensitive, rapid, non-invasive methods of monitoring organ transplant patients for immunocompetence that are sensitive, rapid and inexpensive.

SUMMARY OF THE INVENTION

The invention provides methods, devices, compositions and kits for analysis of the microbiome or individual components thereof in an individual. The methods find use in a determination of infection, in analysis of the microbiome structure, in determining the immunocompetence of an individual, and the like. In some embodiments, the invention provides methods of determining the presence and prevalence of microorganisms in an individual, comprising the steps of: (i) providing a sample of cell-free nucleic acids, i.e. DNA and/or RNA from an individual; (ii) performing high-throughput sequencing, for example from about $10^5$, and up to about $10^9$ or more reads per sample; (iii) performing bioinformatics analysis to subtract host sequences, i.e. human, cat, dog, etc. from the analysis; and (iv) determining the presence and prevalence of microbial sequences, for example by a comparison of the coverage of sequences mapping to a microbial reference sequence to coverage of the host reference sequence.

The subtraction of host sequences may include the step of identifying a reference host sequence, and masking microbial sequences or microbial mimicking sequences present in the reference host genome. Similarly, determining the presence of a microbial sequence by comparison to a microbial reference sequence may include the step of identifying a reference microbial sequence, and masking host sequences or host mimicking sequences present in the reference microbial genome.

A feature of the invention is the unbiased analysis of cell-free nucleic acids from an individual. The methods of the invention generally include an unbiased amplification step, for example by performing PCR with universal primers, or by ligation of adapters to the nucleic acid and amplifying with primers specific for the adaptors. The methods of the invention are typically performed in the absence of sequence specific amplification of microbial sequences. A benefit to this approach is that analysis then includes all available microbiome sequences, however it requires bioinformatics analysis to identify sequences of interest in a complex dataset predominated by host sequences.

A further benefit of the methods of the invention is the ability to provide a rapid assessment of an individual microbiome, for example analysis may be completed in less than about 3 days, less than about 2 days, less than one day, e.g. less than about 24 hours, less than about 20 hours, less than about 18 hours, less than about 14 hours, less than about 12 hours.

The analysis of the presence and prevalence of microbial sequences can be used to provide a determination on infection, of response to therapy, including anti-microbial treatment such as treatment with antibiotics, anti-viral agents, immunization, passive immunotherapy, and the like; diet; immunosuppression, and the like; of response in clinical trials, etc. The information obtained from the analysis may be used to diagnose a condition, to monitor treatment, to select or modify therapeutic regimens, and to optimize therapy. With this approach, therapeutic and/or diagnostic regimens can be individualized and tailored according to the specificity data obtained at different times over the course of treatment, thereby providing a regimen that is individually appropriate. In addition, patient samples can be obtained at any point during the treatment process; following exposure to a pathogen; course of infection, etc. for analysis. The analysis of presence and prevalence of microbial sequences can be provided as a report. The report may be provided to the individual, to a health care professional, etc.

In some embodiments, the cell-free nucleic acid is obtained from a biological sample selected from the group consisting of blood, serum, cerebrospinal fluid, synovial fluid, urine, and stool. The nucleic acid is extracted from the cell free portion of the sample, e.g. serum or plasma portion of blood may be used. In some embodiments, the nucleic acid is selected from the group consisting of double-stranded DNA, single-stranded DNA, single-stranded DNA hairpins, DNA/RNA hybrids, RNA and RNA hairpins. In some embodiments, the nucleic acid is selected from the group consisting of double-stranded DNA, single-stranded DNA and cDNA. In some embodiments, the nucleic acid is mRNA. In some embodiments, the nucleic acid is circulating cell-free DNA.

In some embodiments, the methods comprise quantitating the one or more nucleic acids to provide a determination of prevalence of a microorganism in the sample. In some embodiments, the amount of the one or more nucleic acids above a predetermined threshold value is indicative of infection or altered prevalence. In some embodiments, there are different predetermined threshold values for different microbial organisms. In some embodiments, temporal differences in the amount of the one or more nucleic acids are indicative of changes in infection, altered prevalence, response to therapy, etc.

In some embodiments, the invention provides computer readable mediums comprising: a set of instructions recorded thereon to cause a computer to perform the steps of: (i) receiving high throughput sequencing data from one or more nucleic acids detected in a sample of cell-free nucleic acids from a subject; (ii) performing bioinformatics analysis to subtract host sequences, i.e. human, cat, dog, etc. from the analysis; and (iii) determining the presence and prevalence of microbial sequences, for example by a comparison of the coverage of sequences mapping to a microbial reference sequence to coverage of the host reference sequence.

In some embodiments, the invention provides reagents and kits thereof for practicing one or more of the methods described herein.

In some embodiments, compositions and method are provided for the assessment of immunocompetence of an individual, particularly an individual human, by analysis of the microbiome, for example by analysis of the virome. In some embodiments of the invention, the individual is treated with an immunosuppressive regimen, e.g. drugs, radiation therapy, and the like. In some embodiments the individual is a graft recipient treated with an immunosuppressive regimen. In some embodiments the individual has an autoimmune disease treated with an immunosuppressive regimen. In other embodiments an individual is assessed for immunocompetence in the absence of an immunosuppressive regimen.

In some embodiments a measurement from an individual is taken at two or time points, where a change in virus burden is indicative of a change in immunocompetence. The individual may be treated in accordance with the assessment of immunocompetence, e.g. where an indication of undesirable increased immunocompetence in a transplant patient is treated with increased levels of immunosuppressive agents; or where an undesirable decrease in immunocompetence is treated with therapeutic agents, e.g. anti-viral agents, etc.

Nucleic acid analysis is used to identify and quantify nonhuman cell-free nucleic acids in a sample collected from a patient. The composition of the components of the microbiome is performed as described above. The structure of the viral component of the microbiome (the virome) allows a prediction of immunocompetence. In some embodiments, the methods further comprise establishing a virome profile prior to an immunosuppressive regimen, at the initiation of an immunosuppressive regimen, or during the course of an immunosuppressive regimen, which is used as a reference to changes in the individual virome. In some embodiments the circulating cell-free DNA is annellovirus DNA.

In particular, the load of viruses of the anelloviridae family is a predictor of immune strength, which is correlated with the probability of organ transplant rejection. While other viruses may also be predictive, it is common for patients to be treated with antivirals that affect the load of such viruses.

In some embodiments, the invention provides methods of diagnosing or predicting transplant status or outcome comprising the steps of: (i) providing a sample from a subject who has received a transplant from a donor; (ii) determining the presence or absence of one or more virome nucleic acids; and (iii) diagnosing or predicting transplant status or outcome based on the virome load. In some embodiments, the transplant status or outcome comprises rejection, tolerance, non-rejection based allograft injury, transplant function, transplant survival, chronic transplant injury, or titer pharmacological immunosuppression. In some embodiments, the amount of the one or more nucleic acids above a predetermined threshold value is indicative of viral load and immunocompetence. In some embodiments, the threshold is a normative value for clinically stable post-transplantation patients with no evidence of transplant rejection or other pathologies. In some embodiments, there are different predetermined threshold values for different transplant outcomes or status. In some embodiments, temporal differences in the amount of the one or more nucleic acids are indicative of immunocompetence.

In any of the embodiments described herein, the transplant graft may be any solid organ, bone marrow or skin transplant. In some embodiments, the transplant is selected from the group consisting of kidney transplant, heart transplant, liver transplant, pancreas transplant, lung transplant, intestine transplant and skin transplant.

In some embodiments, the invention provides reagents and kits thereof for practicing one or more of the methods described herein.

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
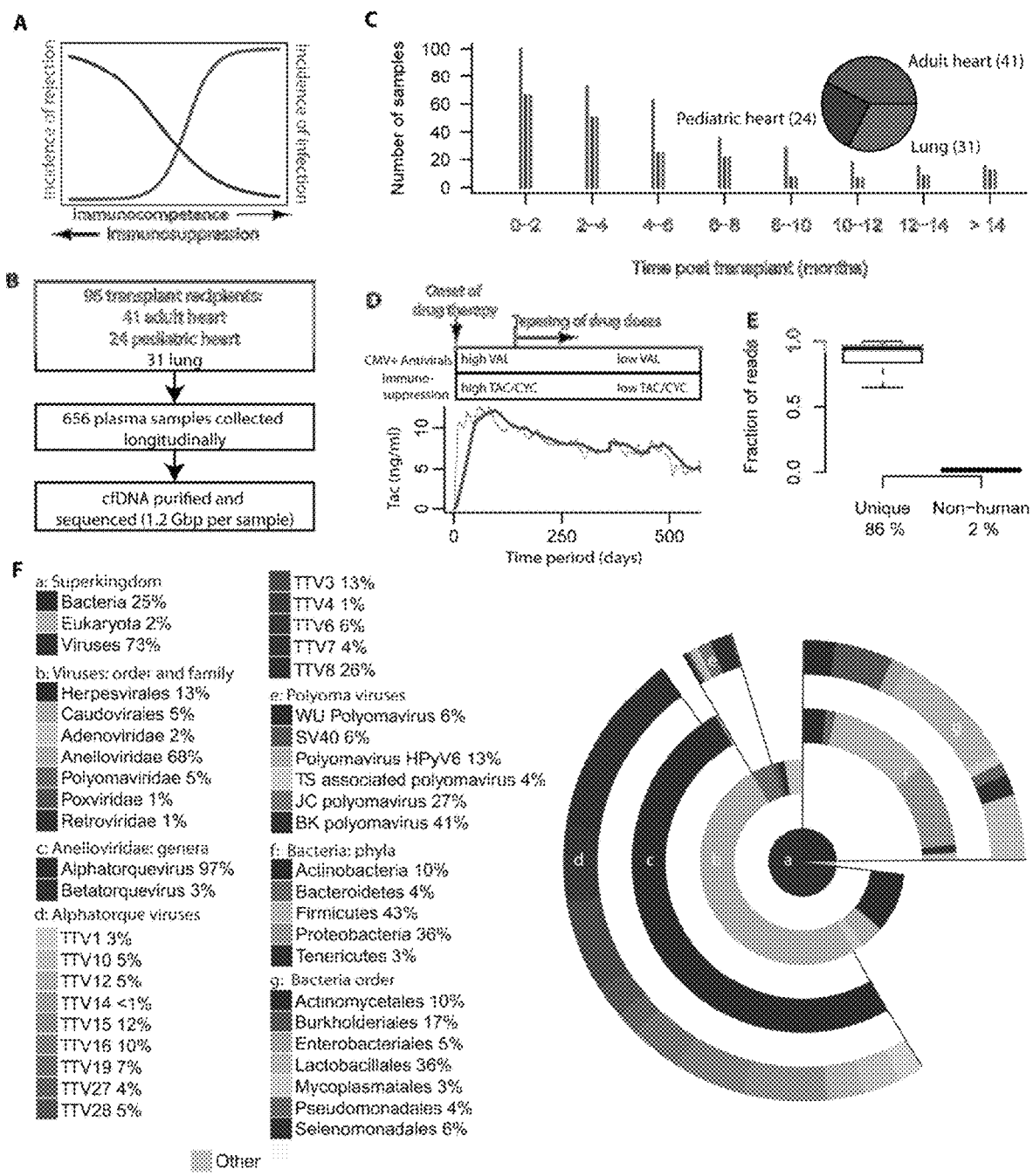
FIG. 1. Study design, read statistics and phylogenetic distribution. A. Immunosuppression reduces the risk of rejection in transplantation but increases the risk of infection. B. Design of study. 656 plasma samples were collected, cell-free DNA was purified and sequenced to an average depth of 1.2 Gbp per sample. C. Number of samples collected as function of time for the different patient groups part of the study. D. Treatment protocol for patients in the study cohort, all patients are treated with maintenance immunosuppression (tacrolimus-based (TAC) for adult heart and lung transplant recipients and cyclosporine (CYC) for pediatric patients). CMV positive (donor or recipient, CMV+) transplant cases are treated with anti-CMV prophylaxis, valganciclovir (VAL). Mean level of tacrolimus measured in blood of transplant recipients treated with a TAC-based protocol (dashed line actual, solid line window average filter). E. Fraction of reads that remain after filtering of lower quality and duplicate reads (mean 86%, left) and after removal of human and low complexity reads (mean 2%, right). F. Relative genomic abundance at different levels of taxonomic classification after removal of human reads (average over all samples from all organ transplant recipients (n=656)).

Reference will now be made in detail to particularly preferred embodiments of the invention. Examples of the preferred embodiments are illustrated in the following Examples section.

Unless defined otherwise, all technical and scientific terms used herein have the same meaning as is commonly understood by one of skill in the art to which this invention belongs. All patents and publications referred to herein are incorporated by reference in their entirety.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The invention provides methods, devices, compositions and kits for analysis of the microbiome or individual components thereof in an individual. The methods find use in a determination of infection, in analysis of the microbiome structure, in determining the immunocompetence of an individual, and the like. In some embodiments, the invention provides methods of determining whether a patient or subject is displaying immunocompetence. The term "individual", "patient" or "subject" as used herein includes humans as well as other mammals.

Definitions

As used herein the term "diagnose" or "diagnosis" of a status or outcome includes predicting or diagnosing the status or outcome, determining predisposition to a status or outcome, monitoring treatment of patient, diagnosing a therapeutic response of a patient, and prognosis of status or outcome, progression, and response to particular treatment.

Microbiota. As used herein, the term microbiota refers to the set of microorganisms present within an individual, usually an individual mammal and more usually a human individual. The microbiota may include pathogenic species; species that constitute the normal flora of one tissue, e.g. skin, oral cavity, etc., but are undesirable in other tissues, e.g. blood, lungs, etc.; commensal organisms found in the absence of disease; etc. A subset of the microbiome is the virome, which comprises the viral components of the microbiome.

The term "microbiome component" as used herein refers to an individual species, or in the instance of some gut commensal organisms, a genus of microorganisms. The component may be a viral component, a bacterial component, a fungal component, etc.

In a healthy animal, while the internal tissues, e.g. brain, muscle, etc., are normally presumed to be relatively free of bacterial species, the surface tissues, i.e., skin and mucous membranes, are constantly in contact with environmental organisms and become readily colonized by various microbial species. The mixture of organisms known or presumed to be found in humans at any anatomical site is referred to as the "indigenous microbiota", including various components of the indigenous microbiota. In addition to the indigenous microorganisms are various transient components, such as pathogenic or opportunistic infections. Reference sequences of organisms described below are publicly available and known in the for, example at the Genbank database.

The intestinal microbiota of humans is dominated by species found within two bacterial phyla: members of the Bacteroidetes and Firmicutes make up >90% of the bacterial population. Actinobacteria (e.g., members of the *Bifidobacterium* genus) and Proteobacteria among several other phyla are less prominently represented. Common species of interest include prominent or less abundant members of this community, and may comprise, without limitation, *Bacteroides thetaiotaomicron; Bacteroides caccae; Bacteroides*

*fragilis*; *Bacteroides melaninogenicus*; *Bacteroides oralis*; *Bacteroides uniformis*; *Lactobacillus*; *Clostridium perfringens*; *Clostridium septicum*; *Clostridium tetani*; *Bifidobacterium bifidum*; *Staphylococcus aureus*; *Enterococcus faecalis*; *Escherichia coli*; *Salmonella enteritidis*; *Klebsiella* sp.; *Enterobacter* sp.; *Proteus mirabilis*; *Pseudomonas aeruginosa*; *Peptostreptococcus* sp.; *Peptococcus* sp., *Faecalibacterium* sp. *Roseburia* sp.; *Ruminococcus* sp.; *Dorea* sp.; *Alistipes* sp.; etc.

In the skin microbiome most bacteria fall into four different phyla: Actinobacteria, Firmicutes, Bacteroidetes and Proteobacteria. Microorganisms that are generally regarded as skin colonizers include coryneforms of the phylum Actinobacteria (the genera *Corynebacterium*, *Propionibacterium*, such as *Propionibacterium acnes*; and *Brevibacterium*), the genus *Micrococcus* and *Staphylococcus* spp. The most commonly isolated fungal species are *Malassezia* spp., which are especially prevalent in sebaceous areas. The *Demodex* mites (such as *Demodex folliculorum* and *Demodex brevis*) may also be present. Other types of fungi that are thought to grow on the skin, include Debaryomyces and *Cryptococcus* spp. As non-commensals, burn wounds commonly become infected with *S. pyogenes*, *Enterococcus* spp. or *Pseudomonas aeruginosa*, and can also become infected with fungi and/or viruses. *S. epidermidis* is a very common skin commensal, but it is also the most frequent cause of hospital-acquired infection on in-dwelling medical devices such as catheters or heart valves. For a review, see Nat Rev Microbiol. (2011) April; 9(4): 244-53.

Pathogenic species may be bacteria, virus, protozoan parasites, fungal species, etc. Bacteria include *Brucella* sp., *Treponema* sp., *Mycobacterium* sp., *Listeria* sp., *Legionella* sp., *Helicobacter* sp, *Streptococcus* sp, *Neisseria* sp, *Clostridium* sp, *Staphylococcus* sp. or *Bacillus* sp.; including without limitation *Treponema pallidum*, *Mycobacterium tuberculosis*, *Mycobacterium leprae*, *Listeria monocytogenes*, *Legionella pneumophila*, *Helicobacter pylori*, *Streptococcus pneumoniae*, *Neisseria meningitis*, *Clostridium novyi*, *Clostridium botulinum*, *Staphylococcus aureus*, *Bacillus anthracis*, etc.

Parasite pathogens include *Trichomonas*, *Toxoplasma*, *Giardia*, *Cryptosporidium*, *Plasmodium*, *Leishmania*, *Trypanosoma*, *Entamoeba*, *Schistosoma*, *Filariae*, *Ascaria*, *Fasciola*; including without limitation *Trichomonas vaginalis*, *Toxoplasma gondii*, *Giardia intestinalis*, *Cryptosporidium parva*, *Plasmodium falciparum*, *Trypanosoma cruzi*, *Entamoeba histolytica*, *Giardia lamblia*, *Fasciola hepatica*, etc.

Viruses that infect humans include, for example, Adeno-associated virus; Aichi virus; Australian bat lyssavirus; BK polyomavirus; Banna virus; Barmah forest virus; Bunyamwera virus; Bunyavirus La Crosse; Bunyavirus snowshoe hare; Cercopithecine herpesvirus; Chandipura virus; Chikungunya virus; Cosavirus A; Cowpox virus; Coxsackievirus; Crimean-Congo hemorrhagic fever virus; Dengue virus; Dhori virus; Dugbe virus; Duvenhage virus; Eastern equine encephalitis virus; Ebolavirus; Echovirus; Encephalomyocarditis virus; Epstein-Barr virus; European bat lyssavirus; GB virus C/Hepatitis G virus; Hantaan virus; Hendra virus; Hepatitis A virus; Hepatitis B virus; Hepatitis C virus; Hepatitis E virus; Hepatitis delta virus; Horsepox virus; Human adenovirus; Human astrovirus; Human coronavirus; Human cytomegalovirus; Human enterovirus 68, 70; Human herpesvirus 1; Human herpesvirus 2; Human herpesvirus 6; Human herpesvirus 7; Human herpesvirus 8; Human immunodeficiency virus; Human papillomavirus 1; Human papillomavirus 2; Human papillomavirus 16,18; Human parainfluenza; Human parvovirus B19; Human respiratory syncytial virus; Human rhinovirus; Human SARS coronavirus; Human spumaretrovirus; Human T-lymphotropic virus; Human torovirus; Influenza A virus; Influenza B virus; Influenza C virus; Isfahan virus; JC polyomavirus; Japanese encephalitis virus; Junin arenavirus; KI Polyomavirus; Kunjin virus; Lagos bat virus; Lake Victoria marburgvirus; Langat virus; Lassa virus; Lordsdale virus; Louping ill virus; Lymphocytic choriomeningitis virus; Machupo virus; Mayaro virus; MERS coronavirus; Measles virus; Mengo encephalomyocarditis virus; Merkel cell polyomavirus; Mokola virus; Molluscum contagiosum virus; Monkeypox virus; Mumps virus; Murray valley encephalitis virus; New York virus; Nipah virus; Norwalk virus; O'nyong-nyong virus; Orf virus; Oropouche virus; Pichinde virus; Poliovirus; Punta toro phlebovirus; Puumala virus; Rabies virus; Rift valley fever virus; Rosavirus A; Ross river virus; Rotavirus A; Rotavirus B; Rotavirus C; Rubella virus; Sagiyama virus; Salivirus A; Sandfly fever sicilian virus; Sapporo virus; Semliki forest virus; Seoul virus; Simian foamy virus; Simian virus 5; Sindbis virus; Southampton virus; St. louis encephalitis virus; Tick-borne powassan virus; Torque teno virus; Toscana virus; Uukuniemi virus; Vaccinia virus; Varicella-zoster virus; Variola virus; Venezuelan equine encephalitis virus; Vesicular stomatitis virus; Western equine encephalitis virus; WU polyomavirus; West Nile virus; Yaba monkey tumor virus; Yaba-like disease virus; Yellow fever virus; Zika virus;

Anelloviridae. The Anelloviridae family consists of non-enveloped, circular, single-stranded DNA viruses. Three genera of anellovirus are known to infect humans, named TTV, TTMDV, and TTMV.

Torque Teno Virus (TTV) is a non-enveloped, single-stranded DNA virus with a circular, negative-sense genome. A smaller virus, which was subsequently named Torque Teno-like Mini Virus (TTMV) has also been characterized, and a third virus with a genomic size in between that of TTV and TTMV was discovered and subsequently named Torque Teno-like Midi Virus (TTMDV). Recent changes in nomenclature have classified the three anelloviruses able to infect humans into Alphatorquevirus (TTV), Betatorquevirus (TTMV), and Gammatorquevirus (TTMDV) Genera of the Anelloviridae family of viruses. To date anelloviruses are still considered "orphan" viruses waiting to be linked to human disease.

The human anelloviruses differ in genome size ranging from 3.8-3.9 kb for TTV, 3.2 kb for TTMDV, and 2.8-2.9 kb for TTMV. A characteristic feature of anelloviruses is the extreme diversity found both within and between anellovirus species; they can exhibit as much as 33%-50% divergence at the nucleotide level. Despite the nucleotide sequence diversity, anelloviruses share conserved genomic organization, transcriptional profiles, a non-coding GC rich region, and sequence motifs resulting in shared virion structure and gene functions.

Anellovirus infections are highly prevalent in the general population. A study in Japan found that 75-100% of patients tested were infected with at least one of the three human anelloviruses, and many were infected with multiple species. Anelloviruses can infect young children, with the earliest documented infections occurring within the first months of life. These viruses have been found in nearly every body site, fluid, and tissue tested including blood plasma, serum, peripheral blood mononuclear cells (PBMCs), nasopharyngeal aspirates, bone marrow, saliva, breast milk, feces, as well as various tissues including thyroid gland, lymph node, lung, liver, spleen, pancreas, and kidney. The replication dynamics of anelloviruses are virtually unknown because of the inability to propagate these viruses in culture. Positive-strand TTV DNA, indicative of local viral replication, has been described in hepatocytes, bone marrow cells, and circulating PBMCs.

Anelloviruses are spread primarily through fecal-oral transmission, although mother-child and respiratory tract transmissions have also been reported. There are conflicting reports regarding the presence of TTV in cord blood specimens.

Reference sequences for anellovirus may be accessed at Genbank, e.g. Torque teno mini virus 1, Accession: NC_014097.1; Torque teno mini virus 6, Accession: NC_014095.1; Torque teno midi virus 2, Accession: NC_014093.1; Torque teno midi virus 1, Accession: NC_009225.1; Torque teno virus 3, Accession: NC_014081.1; Torque teno virus 19, Accession: NC_014078.1; Torque teno mini virus 8, Accession: NC_014068.1.

The term "antibiotic" as used herein includes all commonly used bacteristatic and bactericidal antibiotics, usually those administered orally. Antibiotics include aminoglycosides, such as amikacin, gentamicin, kanamycin, neomycin, streptomycin, and tobramycin; cephalosporins, such as cefamandole, cefazolin, cephalexin, cephaloglycin, cephaloridine, cephalothin, cephapirin, and cephradine; macrolides, such as erythromycin and troleandomycin; penicillins, such as penicillin G, amoxicillin, ampicillin, carbenicillin, cloxacillin, dicloxacillin, methicillin, nafcillin, oxacillin, phenethicillin, and ticarcillin; polypeptide antibiotics, such as bacitracin, colistimethate, colistin, polymyxin B; tetracyclines, such as chlortetracycline, demeclocycline, doxycycline, methacycline, minocycline, tetracycline, and oxytetracycline; and miscellaneous antibiotics such as chloramphenicol, clindamycin, cycloserine, lincomycin, rifampin, spectinomycin, vancomycin, and viomycin. Additional antibiotics' are described in "Remington's Pharmaceutical Sciences," 16th Ed., (Mack Pub. Co., 1980), pp. 1121-1178.

Antiviral agents. Individuals may receive antiviral therapy, which will alter the viral load for those viruses affected by the therapy. Examples of viral infections thus treated include HIV, Bowenoid Papulosis, Chickenpox, Childhood HIV Disease, Human Cowpox, Hepatitis C, Dengue, Enteroviral, Epidermodysplasia Verruciformis, Erythema Infectiosum (Fifth Disease), Giant Condylomata Acuminata of Buschke and Lowenstein, Hand-Foot-and-Mouth Disease, Herpes Simplex, Herpes Virus 6, Herpes Zoster, Kaposi Varicelliform Eruption, Rubeola Measles, Milker's Nodules, Molluscum Contagiosum, Monkeypox, Orf, Roseola Infantum, Rubella, Smallpox, Viral Hemorrhagic Fevers, Genital Warts, and Nongenital Warts.

Antiviral agents include azidouridine, anasmycin, amantadine, bromovinyldeoxusidine, chlorovinyldeoxusidine, cytarbine, didanosine, deoxynojirimycin, dideoxycitidine, dideoxyinosine, dideoxynucleoside, desciclovir, deoxyacyclovir, edoxuidine, enviroxime, fiacitabine, foscamet, fialuridine, fluorothymidine, floxuridine, hypericin, interferon, interleukin, isethionate, nevirapine, pentamidine, ribavirin, rimantadine, stavirdine, sargramostin, suramin, trichosanthin, tribromothymidine, trichlorothymidine, vidarabine, zidoviridine, zalcitabine and 3-azido-3-deoxythymidine, and analogs, derivatives, pharmaceutically acceptable salts, esters, prodrugs, codrugs, and protected forms thereof.

Immunosuppression or immunosuppressive regimen, as used herein, refers to the treatment of an individual, for example a graft recipient with agents to diminish the immune responses of the host immune system against autoantigens or graft. Exemplary immunosuppression regimens are described in more detail herein.

Primary immunosuppressive agents include calcineurin inhibitors, which combine with binding proteins to inhibit calcineurin activity, and which include, for example, tacrolimus, cyclosporine A, etc. Levels of both cyclosporine and tacrolimus must be carefully monitored. Initially, levels can be kept in the range of 10-20 ng/mL, but, after 3 months, levels may be kept lower (5-10 ng/mL) to reduce the risk of nephrotoxicity.

Adjuvant agents are usually combined with a calcineurin inhibitor and include steroids, azathioprine, mycophenolate mofetil, and sirolimus. Protocols of interest include a calcineurin inhibitor with mycophenolate mofetil. The use of adjuvant agents allows clinicians to achieve adequate immunosuppression while decreasing the dose and toxicity of individual agents. Mycophenolate mofetil in kidney transplant recipients has assumed an important role in immunosuppression after several clinical trials have shown a markedly decreased prevalence of acute cellular rejection compared with azathioprine and a reduction in 1-year treatment failures.

Antibody-based therapy may use monoclonal (eg, muromonab-CD3) or polyclonal antibodies or anti-CD25 antibodies (eg, basiliximab, daclizumab) and is administered in the early post-transplant period (up to 8 wk). Antibody-based therapy allows for avoidance or dose reduction of calcineurin inhibitors, possibly reducing the risk of nephrotoxicity. The adverse effect profile of the polyclonal and monoclonal antibodies limits their use in some patients.

The term "nucleic acid" used herein refers to a polynucleotide comprising two or more nucleotides. It may be DNA or RNA. A "variant" nucleic acid is a polynucleotide having a nucleotide sequence identical to that of its original nucleic acid except having at least one nucleotide modified, for example, deleted, inserted, or replaced, respectively. The variant may have a nucleotide sequence at least about 80%, 90%, 95%, or 99%, identity to the nucleotide sequence of the original nucleic acid.

Circulating, or cell-free, DNA was first detected in human blood plasma in 1948. (Mandel, P. Metais, P., C R Acad. Sci. Paris, 142, 241-243 (1948)) Since then, its connection to disease has been established in several areas. (Tong, Y. K. Lo, Y. M., Clin Chim Acta, 363, 187-196 (2006)) Studies reveal that much of the circulating nucleic acids in blood arise from necrotic or apoptotic cells (Giacona, M. B., et al., Pancreas, 17, 89-97 (1998)) and greatly elevated levels of nucleic acids from apoptosis is observed in diseases such as cancer. (Giacona, M. B., et al., Pancreas, 17, 89-97 (1998); Fournie, G. J., et al., Cancer Lett, 91, 221-227 (1995)). Particularly for cancer, where the circulating DNA bears hallmark signs of the disease including mutations in oncogenes, microsatellite alterations, and, for certain cancers, viral genomic sequences, DNA or RNA in plasma has become increasingly studied as a potential biomarker for disease. For example, Diehl et al recently demonstrated that a quantitative assay for low levels of circulating tumor DNA in total circulating DNA could serve as a better marker for detecting the relapse of colorectal cancer compared with carcinoembryonic antigen, the standard biomarker used clinically. (Diehl, F., et al., Proc Natl Acad Sci, 102, 16368-16373 (2005); Diehl, F., et al., Nat Med, 14, 985-990 (2008)). Maheswaran et al reported the use of genotyping of circulating cells in plasma to detect activating mutations in epidermal growth factor receptors in lung cancer patients that would affect drug treatment. (Maheswaran, S., et al., N Engl J Med, 359, 366-377 (2008)) These results collectively establish circulating DNA free in plasma as a useful species in cancer detection and treatment. Circulating DNA has also been useful in healthy patients for fetal diagnostics, with fetal DNA circulating in maternal blood serving as a marker for gender, rhesus D status, fetal aneuploidy, and sex-linked disorders. Fan et al recently demonstrated a strategy for detecting fetal aneuploidy by shotgun sequencing of cell-free DNA taken from a maternal blood sample, a methodology that can replace more invasive and risky techniques such as amniocentesis or chorionic villus sampling. (Fan, H. C., Blumenfeld, Y. J., Chitkara, U., Hudgins, L., Quake, S. R., Proc Natl Acad Sci, 105, 16266-16271 (2008)).

The term "derived from" used herein refers to an origin or source, and may include naturally occurring, recombinant, unpurified or purified molecules. A nucleic acid derived from an original nucleic acid may comprise the original nucleic acid, in part or in whole, and may be a fragment or variant of the original nucleic acid. A nucleic acid derived from a biological sample may be purified from that sample.

A "target nucleic acid" in the method according to the present invention is a nucleic acid, DNA or RNA, to be detected. A target nucleic acid derived from an organism is a polynucleotide that has a sequence derived from that of the organism and is specific to the organism. A target nucleic acid derived from a pathogen refers to a polynucleotide having a polynucleotide sequence derived from that specific the pathogen.

In some embodiments, less than 1 µg, 5 µg, 10 µg, 20 µg, 30 µg, 40 µg, 50 µg, 100 µg, 200 µg, 500 µg, 1 ng, 5 ng, 10 ng, 20 ng, 30 ng, 40 ng, 50 ng, 100 ng, 200 ng, 500 ng, 1 µg, 5 µg, 10 µg, 20 µg, 30 µg, 40 µg, 50 µg, 100 µg, 200 µg, 500 µg or 1 mg of nucleic acids are obtained from the sample for analysis. In some cases, about 1-5 µg, 5-10 µg, 10-100 µg, 100 µg-1 ng, 1-5 ng, 5-10 ng, 10-100 ng, 100 ng-1 µg of nucleic acids are obtained from the sample for analysis.

In some embodiments, the methods described herein are used to detect and/or quantify nucleic acid sequences that correspond to a microbe of interest, or a microbiome of organisms. The methods described herein can analyze at least 1; 2; 3; 4; 5; 10, 20; 50; 100; 200; 500; 1,000; 2,000; 5,000; 10,000, 20,000; 50,000; 100,000; 200,000; 300,000; 400,000; 500,000; 600,000; 700,000; 800,000; 900,000; $10^6$, $5 \times 10^6$, $10^7$, $5 \times 10^7$, $10^8$, $5 \times 10^8$, $10^9$ or more sequence reads.

In some embodiments, the methods described herein are used to detect and/or quantify gene expression, e.g. by determining the presence of mRNA from a microorganism in relation to DNA from that microorganism. In some embodiments, the methods described herein provide high discriminative and quantitative analysis of multiple genes. The methods described herein can discriminate and quantitate the expression of at least 1, 2, 3, 4, 5, 10, 20, 50, 100, 200, 500, 1,000, 2,000, 5,000, 10,000, 20,000, 50,000, 100,000, or more different target nucleic acids.

A sample containing cell-free nucleic acids is obtained from a subject. Such subject can be a human, a domesticated animal such as a cow, chicken, pig, horse, rabbit, dog, cat, goat, etc. In some embodiments, the cells used in the present invention are taken from a patient. Samples include, for example, the acellular fraction of whole blood, sweat, tears, saliva, ear flow, sputum, lymph, bone marrow suspension, lymph, urine, saliva, semen, vaginal flow, cerebrospinal fluid, brain fluid, ascites, milk, secretions of the respiratory, intestinal or genitourinary tracts fluid, a lavage of a tissue or organ (e.g. lung) or tissue which has been removed from organs, such as breast, lung, intestine, skin, cervix, prostate, pancreas, heart, liver and stomach. Such samples can be separated by centrifugation, elutriation, density gradient separation, apheresis, affinity selection, panning, FACS, centrifugation with Hypaque, etc. Once a sample is obtained, it can be used directly, frozen, or maintained in appropriate culture medium for short periods of time.

To obtain a blood sample, any technique known in the art may be used, e.g. a syringe or other vacuum suction device. A blood sample can be optionally pre-treated or processed prior to use. A sample, such as a blood sample, can be analyzed under any of the methods and systems herein within 1 week, 6 days, 5 days, 4 days, 3 days, 2 days, 1 day, 12 hrs, 6 hrs, 3 hrs, 2 hrs, or 1 hr from the time the sample is obtained. When obtaining a sample from a subject (e.g., blood sample), the amount can vary depending upon subject size and the condition being screened. In some embodiments, up to 50, 40, 30, 20, 10, 9, 8, 7, 6, 5, 4, 3, 2, or 1 mL of a sample is obtained. In some embodiments, 1-50, 2-40, 3-30, or 4-20 mL of sample is obtained. In some embodiments, more than 5, 10, 15, 20, 25, 30, 35, 40, 45, 50, 55, 60, 65, 70, 75, 80, 85, 90, 95 or 100 mL of a sample is obtained.

The cell-free fraction is preferably blood serum or blood plasma. The term "cell-free fraction" of a biological sample used herein refers to a fraction of the biological sample that is substantially free of cells. The term "substantially free of cells" used herein refers to a preparation from the biological sample comprising fewer than about 20,000 cells per ml, preferably fewer than about 2,000 cells per ml, more preferably fewer than about 200 cells per ml, most preferably fewer than about 20 cells per ml. In contrast to certain prior art methods, genomic DNA is not excluded from the acellular sample, and typically comprises from about 50% to about 90% of the nucleic acids that are present in the sample.

The method of the present invention may further comprise preparing a cell-free fraction from a biological sample. The cell-free fraction may be prepared using conventional techniques known in the art. For example, a cell-free fraction of a blood sample may be obtained by centrifuging the blood sample for about 3-30 min, preferably about 3-15 min, more preferably about 3-10 min, most preferably about 3-5 min, at a low speed of about 200-20,000 g, preferably about 200-10,000 g, more preferably about 200-5,000 g, most preferably about 350-4,500 g. The biological sample may be obtained by ultrafiltration in order to separate the cells and their fragments from a cell-free fraction comprising soluble DNA or RNA. Conventionally, ultrafiltration is carried out using a 0.22 µm membrane filter.

The method of the present invention may further comprise concentrating (or enriching) the target nucleic acid in the cell-free fraction of the biological sample. The target nucleic acid may be concentrated using conventional techniques known in the art, such as solid phase absorption in the presence of a high salt concentration, organic extraction by phenol-chloroform followed by precipitation with ethanol or isopropyl alcohol, or direct precipitation in the presence of a high salt concentration or 70-80% ethanol or isopropyl alcohol. The concentrated target nucleic acid may be at least about 2, 5, 10, 20 or 100 times more concentrated than that in the cell-free fraction. The target nucleic acid, whether or not concentrated, may be used for amplification according to the method of the present invention.

In some embodiments the invention provides methods for diagnosis or prediction of transplant rejection. The term "transplant rejection" encompasses both acute and chronic transplant rejection. "Acute rejection or AR" is the rejection by the immune system of a tissue transplant recipient when the transplanted tissue is immunologically foreign. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery. Generally, acute rejection can be inhibited or suppressed with immunosuppressive drugs such as rapamycin, cyclosporin A, anti-CD40L monoclonal antibody and the like.

"Chronic transplant rejection or CR" generally occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome. Chronic rejection can also be characterized by ischemic insult, denervation of the transplanted tissue, hyperlipidemia and hypertension associated with immunosuppressive drugs.

In some embodiments, the invention further includes methods for determining the effectiveness of an immunosuppressive regimen for a subject who has received a transplant, e.g., an allograft.

Certain embodiments of the invention provide methods of predicting transplant survival in a subject that has received a transplant. The invention provides methods of diagnosing or predicting whether a transplant in a transplant patient or subject will survive or be lost. In certain embodiments, the invention provides methods of diagnosing or predicting the presence of long-term graft survival. By "long-term" graft survival is meant graft survival for at least about 5 years beyond current sampling, despite the occurrence of one or more prior episodes of acute rejection. In certain embodiments, transplant survival is determined for patients in which at least one episode of acute rejection has occurred. As such, these embodiments provide methods of determining or predicting transplant survival following acute rejection. Transplant survival is determined or predicted in certain embodiments in the context of transplant therapy, e.g., immunosuppressive therapy, where immunosuppressive therapies are known in the art. In yet other embodiments, methods of determining the class and/or severity of acute rejection (and not just the presence thereof) are provided.

As in known in the transplantation field, the transplant organ, tissue or cell(s) may be allogeneic or xenogeneic, such that the grafts may be allografts or xenografts. A feature of the graft tolerant phenotype detected or identified by the subject methods is that it is a phenotype which occurs without immunosuppressive therapy, i.e., it is present in a host that is not undergoing immunosuppressive therapy such that immunosuppressive agents are not being administered to the host. The transplant graft may be any solid organ and skin transplant. Examples of organ transplants that can be analyzed by the methods described herein include but are not limited to kidney transplant, pancreas transplant, liver transplant, heart transplant, lung transplant, intestine transplant, pancreas after kidney transplant, and simultaneous pancreas-kidney transplant.

Microbiome Detection and Analysis

The methods of the invention involve high throughput sequencing of a cell-free nucleic acid sample from an individual, followed by bioinformatics analysis to determine the presence and prevalence of microbial sequences, which sequences may be from indigenous organisms, e.g. the normal microbiome of gut, skin, etc., or may be non-indigenous, e.g. opportunistic, pathogenic, etc. infections. Analysis may be performed for the complete microbiome, or for components there, for example the virome, bacterial microbiome, fungal microbiome, protozoan microbiome, etc. Examples of nucleic acids include, but are not limited to double-stranded DNA, single-stranded DNA, single-stranded DNA hairpins, DNA/RNA hybrids, RNA (e.g. mRNA or miRNA) and RNA hairpins. In some embodiments, the nucleic acid is DNA. In some embodiments, the nucleic acid is RNA. For instance, cell-free RNA and DNA are present in human plasma.

Genotyping microbiome nucleic acids, and/or detection, identification and/or quantitation of the microbiome-specific nucleic acids generally include an initial step of amplification of the sample, although there may be instances where sufficient cell free nucleic acids are available and can be directly sequenced. When the nucleic acid is RNA, the amplification step may be preceded by a reverse transcriptase reaction to convert the RNA into DNA. Preferably the amplification is unbiased, that is the primers for amplification are universal primers, or adaptors are ligated to the nucleic acids being analyzed, and amplification primers are specific for the adaptors. Examples of PCR techniques include, but are not limited, to hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that may be used to amplify specific polymorphic loci include those described in, U.S. Pat. Nos. 5,242,794, 5,494,810, 4,988,617 and 6,582,938.

Following amplification, the amplified nucleic acid is sequenced. Sequencing can be accomplished using high-throughput systems some of which allow detection of a sequenced nucleotide immediately after or upon its incorporation into a growing strand, i.e., detection of sequence in red time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; with each read being at least 50, at least 60, at least 70, at least 80, at least 90, at least 100, at least 120 or at least 150 bases per read. Sequencing can be performed using nucleic acids described herein such as genomic DNA, cDNA derived from RNA transcripts or RNA as a template.

In some embodiments, high-throughput sequencing involves the use of technology available by Helicos BioSciences Corporation (Cambridge, Mass.) such as the Single Molecule Sequencing by Synthesis (SMSS) method. SMSS is unique because it allows for sequencing an entire genome with no pre amplification step needed. Thus, distortion and nonlinearity in the measurement of nucleic acids are reduced. SMSS is described in part in US Publication Application Nos. 2006002471 I; 20060024678; 20060012793; 20060012784; and 20050100932.

In some embodiments, high-throughput sequencing involves the use of technology available by 454 Life-sciences, Inc. (Branford, Conn.) such as the Pico Titer Plate device, which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density pricolitre reactors", Nature, doi: 10.1038/nature03959; and well as in US Publication Application Nos. 20020012930; 20030058629; 20030100102; 20030148344; 20040248161; 20050079510, 20050124022; and 20060078909.

In some embodiments, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 2004010613 0; 20030064398; 20030022207; and Constans, A, The Scientist 2003, 17(13):36.

In some embodiments of this aspect, high-throughput sequencing of RNA or DNA can take place using Any-Dot.chips (Genovoxx, Germany), which allows for the monitoring of biological processes (e.g., miRNA expression or allele variability (SNP detection). In particular, the Any-Dot-chips allow for 10×-50× enhancement of nucleotide fluorescence signal detection. AnyDot.chips and methods for using them are described in part in International Publication Application Nos. WO 02088382, WO 03020968, WO 0303 1947, WO 2005044836, PCTEP 05105657, PCMEP 05105655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al, Science 24 Mar. 2000; and M. J, Levene, et al. Science 299:682-686, January 2003; as well as US Publication Application No. 20030044781 and 2006/0078937. Overall such system involve sequencing a target nucleic acid molecule having a plurality of bases by the temporal addition of bases via a polymerization reaction that is measured on a molecule of nucleic acid, i.e., the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishably type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

In some embodiments, shotgun sequencing is performed. In shotgun sequencing, DNA is broken up randomly into numerous small segments, which are sequenced using the chain termination method to obtain reads. Multiple overlapping reads for the target DNA are obtained by performing several rounds of this fragmentation and sequencing. Computer programs then use the overlapping ends of different reads to assemble them into a continuous sequence.

In some embodiments, the invention provides methods for detection and quantitation of microbial sequences using sequencing. In this case, one can estimate the sensitivity of detection. There are two components to sensitivity: (i) the number of molecules analyzed (depth of sequencing) and (ii) the error rate of the sequencing process. Regarding the depth of sequencing, a frequent estimate for the variation between individuals is that about one base per thousand differs. Currently, sequencers such as the Illumina Genome Analyzer have read lengths exceeding 36 base pairs. While the fraction of host DNA in the blood may be variable depending on the status of the individual, one can take 90% as a baseline estimate. At this fraction of donor DNA, approximately one in 10 molecules analyzed will be microbial. On the Genome Analyzer one can obtain about 10 million molecules per analysis channel and there are 8 analysis channels per instrument run. Therefore, if one sample is loaded per channel, one should be able to detect about $10^6$ molecules that can be identified as microbial and informative as to the status of the microbiome. Higher sensitivity can be achieved simply by sequencing more molecules, i.e. using more channels.

The sequencing error rate also affects the sensitivity of this technique. Typical sequencing error rates for base substitutions vary between platforms, but are between 0.5-1.5%. This places a potential limit on sensitivity of 0.16 to 0.50%. However, it is possible to systematically lower the sequencing error rate by resequencing the sample template multiple times, as has been demonstrated by Helicos Bio-Sciences (Harris, T. D., et al., Science, 320, 106-109 (2008)). A single application of resequencing would reduce the expected error rate.

Following sequencing, the dataset of sequences is uploaded to a data processor for bioinformatics analysis to subtract host sequences, i.e. human, cat, dog, etc. from the analysis; and determine the presence and prevalence of microbial sequences, for example by a comparison of the coverage of sequences mapping to a microbial reference sequence to coverage of the host reference sequence. The subtraction of host sequences may include the step of identifying a reference host sequence, and masking microbial sequences or microbial-mimicking sequences present in the reference host genome. Similarly, determining the presence of a microbial sequence by comparison to a microbial reference sequence may include the step of identifying a reference microbial sequence, and masking host sequences or host-mimicking sequences present in the reference microbial genome.

The dataset is optionally cleaned to check sequence quality, remove remnants of sequencer specific nucleotides (adapter sequences), and merge paired end reads that overlap to create a higher quality consensus sequence with less read errors. Repetitive sequences are identified as those having identical start sites and length, and duplicates may be removed from the analysis.

An important feature of the invention is the subtraction of human sequences from the analysis. As the amplification/sequencing steps are unbiased, the preponderance of sequences in a sample will be host sequences. The subtraction process may be optimized in several ways to improve the speed and accuracy of the process, for example by performing multiple subtractions where the initial alignment is set at a coarse filter, i.e. with a fast aligner, and performing additional alignments with a fine filter, i.e. a sensitive aligner.

The database of reads are initially aligned against a human reference genome, including without limitation Genbank hg19 reference sequences, to bioinformatically subtract the host DNA. Each sequence is aligned with the best fit sequence in the human reference sequence Sequences positively identified as human are bioinformatically removed from the analysis.

The reference human sequence can also be optimized by adding in contigs that have a high hit rate, including without limitation highly repetitive sequence present in the genome that are not well represented in reference databases. It has been observed that of the reads that do not align to hg19, a significant amount is eventually identified as human in a later stage of the pipeline, when a more sensitive aligner is used. Removing these reads earlier in the analysis can be performed by building an expanded human reference. This reference is created by identifying human contigs in a human sequence database other than the reference, e.g. NCBI NT database, that have high coverage after the initial human read subtraction. Those contigs are added to the human reference to create a more comprehensive reference set. Additionally novel assembled human contigs from cohorts studies can be used as a further mask for human-derived reads.

Regions of the human genome reference sequence that contain non-human sequences may be masked, e.g. viral and bacterial sequences that are integrated into the genome of the reference sample. For example, Epstein-Barr Virus (EBV) has about 80% of its genome incorporated into hg19.

Sequence reads identified as non-human are then aligned to a nucleotide database of microbial reference sequences. The database may be selected for those microbial sequences known to be associated with the host, e.g. the set of human commensal and pathogenic microorganisms.

The microbial database may be optimized to mask or remove contaminating sequences. For example it has been observed that many public database entries include artifactual sequences not derived from the microorganism, e.g., primer sequences, host sequences, and other contaminants. It is desirable to perform an initial alignment or plurality of alignments on a database. Regions that show irregularities in read coverage when multiple samples are aligned can be masked or removed as an artifact. The detection of such irregular coverage can be done by various metrics, such as the ratio between coverage of a specific nucleotide and the average coverage of the entire contig within which this nucleotide is found. In general a sequence that is represented as greater than about 5×, about 10×, about 25×, about 50×, about 100× the average coverage of that reference sequence are artifactual. Alternatively a binomial test can be applied to provide a per-base likelihood of coverage given the overall coverage of the contig. Removal of contaminant sequence from reference databases allows accurate identification of microbes. It is a benefit of the methods of the invention that the databases are improved with alignment of samples, e.g. a database my be aligned with 1, 10, 20, 50, 100 or more samples to improve the database prior to commercial or clinical use.

Each high confidence read may align to multiple organisms in the given microbial database. To correctly assign organism abundance based upon this possible mapping redundancy, an algorithm is used to compute the most likely organism an algorithm is selected (for example see Lindner et al. Nucl. Acids Res. (2013) 41 (1): e10). For example GRAMMy or GASiC algorithms can be used to compute the most likely organism that a given read came from. These data provide information regarding the presence of a microbe in the cell-free nucleic acid sample.

These assignments are then totaled and used to compute the estimated number of reads assigned to each organism in a given sample in a determination of the prevalence of the organism in the cell-free nucleic acid sample. The analysis normalizes the counts for the size of the microbial genome to provide a calculation of coverage for the microbe. The normalized coverage for each microbe is compared to the host sequence coverage in the same sample to account for differences in sequencing depth between samples.

The final determination provides a dataset of microbial organisms represented by sequences in the sample, and the prevalence of those microorganisms. These data are optionally aggregated and displayed for ready visualization, e.g. in the form of a report provided to the individual or health care provider; or written in a browser format with hyper-linked data. The coverage estimation can be aggregated with metadata from the sample, and sorted into tables and figures for each sample, or cohort of samples.

Optionally the host sequences that are filtered out can be used for other purposes, e.g. in personalized medicine. For example, certain SNPs in the human genome may allow doctors to identify drug sensitivities for a given patient. The human-derived sequences may reveal integration of viruses into the host's genome (e.g. EBV, HPV, poliomavirus) or be used for synergistic clinical applications (e.g., cell-free tumor DNA may be used to monitor cancer progressing in parallel with infection monitoring in patients that are highly susceptible to infection due to chemotherapy).

Also provided are reagents and kits thereof for practicing one or more of the above-described methods. The subject reagents and kits thereof may vary greatly. Reagents of interest include reagents specifically designed for use in production of the above-described: (i) profiling of a microbiome and an individual; (ii) identification of microbiome profiles; and (ii) detection and/or quantitation of one or more nucleic acids from a microbiome in a sample obtained from an individual. The kits may comprise reagents necessary to perform nucleic acid extraction and/or nucleic acid detection using the methods described herein such as PCR and sequencing. The kit may further comprise a software package for data analysis, which may include reference profiles for comparison with the test profile, and in particular may include reference databases optimized as described above. The kits may comprise reagents such as buffers, and $H_2O$.

Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such kits may also include instructions to access a database. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

Any of the methods above can be performed by a computer program product that comprises a computer executable logic that is recorded on a computer readable medium. For example, the computer program can execute some or all of the following functions: (i) controlling isolation of nucleic acids from a sample, (ii) pre-amplifying nucleic acids from the sample, (iii) amplifying, sequencing or arraying specific regions in the sample, (iv) identifying and quantifying a microbial sequence in the sample, (v) comparing data on a microbe presence or prevalence detected from the sample with a predetermined threshold, (vi) determining infection, microbiome health, immunocompetence status or outcome, (vi) declaring the sample status with respect to infection, microbiome health, immunocompetence, etc.

The computer executable logic can work in any computer that may be any of a variety of types of general-purpose computers such as a personal computer, network server, workstation, or other computer platform now or later developed. In some embodiments, a computer program product is described comprising a computer usable medium having the computer executable logic (computer software program, including program code) stored therein. The computer executable logic can be executed by a processor, causing the processor to perform functions described herein. In other embodiments, some functions are implemented primarily in hardware using, for example, a hardware state machine. Implementation of the hardware state machine so as to perform the functions described herein will be apparent to those skilled in the relevant arts.

The program can provide a method of evaluating microbial status in an individual by accessing data that reflects the profiling of the microbiome and the individual, and/or the quantitation of one or more nucleic acids from the microbiome in the circulation of the individual.

In one embodiment, the computer executing the computer logic of the invention may also include a digital input device such as a scanner. The digital input device can provide information on a nucleic acid, e.g., presence or prevalence In some embodiments, the invention provides a computer readable medium comprising a set of instructions recorded thereon to cause a computer to perform the steps of (i) receiving data from one or more nucleic acids detected in a sample; and (ii) diagnosing or predicting a status based on the microbiome quantitation.

Also provided are databases of microbial reference sequences; and databases of human reference sequences. Such databases will typically comprise optimized datasets as described above.

In some embodiments the methods of the invention provide an individual's status with respect to infection. In some such embodiments, the microbial infection is a pathogen, where any presence of the pathogen sequence indicates a clinically relevant infection. In other embodiments, the prevalence is indicative of microbial load, where a pre-set level is indicative of clinical relevance. In some such embodiments the individual is treated or considered for treatment with an antimicrobial therapy, e.g. antibiotics, passive or active immunotherapy, antivirals, etc. An individual may be tested before therapy, during therapy, and after therapy.

A microbial infection may also be indicated by load for a commensal organism, where the level of a commensal in a blood sample is indicative of intestinal health, e.g. gut lumen breakdown.

A comparison can be made of microbioal RNA, alone or in relation to microbiol DNA, where an excess of RNA for a microbial sequence, e.g. about 5×, 10×, 15×, 20×, 25× the coverage of the microbial DNA is indicative of an active infection. In some embodiments the microbe thus analyzed is one capable of latent infection, e.g. herpesvirus, hepatitis virus, etc.

In other embodiments, an overall estimate of the microbiome is of interest, where the relative presence of prevalence of classes of microorganisms are of interest. It is known in the art that diet and treatment with drugs, e.g. statins, antibiotics, immunosuppressive agents, etc. can affect the overall health of the microbiome, and it is therefor of interest to determine the composition of the microbiome.

In some embodiments, temporal differences in the amount of said one or more nucleic acids from the microbiome can be used to monitor effectiveness of anti-microbial treatment or to select an treatment. For instance, the amount of one or more nucleic acids from the microbiome can be determined before and after an treatment. A decrease in the one or more nucleic acids from the microbe after treatment may indicate that the treatment was successful. Additionally, the amount of one or more nucleic acids from the microbiome can be used to choose between treatments, for examples, treatments of different strengths.

In one aspect the invention provides methods for the diagnosis or prediction of immunocompetence, transplant status or outcome in a subject receiving an immunosuppressive regimen. Following immunosuppression, samples as described above can be drawn from the patient and analyzed for the presence or absence of one or more microbiome, including virome nucleic acids. In some embodiments, the sample is blood, plasma, serum or urine. The proportion and/or amount of microbial nucleic acids can be monitored over time and an increase in this proportion can be used to determine immunocompetence. The quantitation of load may be determined by any suitable method known in the art including those described herein such as sequencing, nucleic acid arrays or PCR.

In some embodiments, the amount of one or more microbiome nucleic acids in a sample from the immunosuppressed recipient is used to determine the transplant status or outcome. Thus, in some embodiments, the methods of the invention further comprise quantitating the one or more nucleic acids from the microbiome. In some embodiments, the amount of one or more nucleic acids from the donor sample is determined as a percentage of total the nucleic acids in the sample. In some embodiments, the amount of one or more nucleic acids from the donor sample is determined as a ratio of the total nucleic acids in the sample. In some embodiments, the amount of one or more nucleic acids from the donor sample is determined as a ratio or percentage compared to one or more reference nucleic acids in the sample. For instance, the amount of one or more nucleic acids from the microbiome can be determined to be 10% of the total nucleic acids in the sample. Alternatively, the amount of one or more nucleic acids from the microbiome can be at a ratio of 1:10 compared to total nucleic acids in the sample. Further, the amount of one or more nucleic acids from the microbiome can be determined to be 10% or at a ratio of 1:10 of a reference gene such a β-globin. In some embodiments, the amount of one or more nucleic acids from the microbiome can be determined as a concentration. For example, the amount of one or more nucleic acids from the donor sample can be determined to be 1 µg/mL.

In some embodiments, the amount of one or more nucleic acids from the microbiome above a predetermined threshold value is indicative of a immunocompetence status. For example, the normative values for clinically stable patients with no evidence of graft rejection or other pathologies can be determined. An increase in the amount of one or more nucleic acids from the microbiome below the normative values for clinically stable post-transplantation patients could indicate a stable outcome. On the other hand, an amount of one or more nucleic acids from the microbiome above or at the normative values for clinically stable post-transplantation patients could indicate increased immunocompetence and risk of graft rejection.

In some embodiments, different predetermined threshold values are indicative of different transplant outcomes or status. For example, as discussed above, an increase in the amount of one or more nucleic acids from the microbiome above the normative values for clinically stable post-transplantation patients could indicate a change in transplant status or outcome such as transplant rejection or transplant injury. However, an increase in the amount of one or more nucleic acids from the microbiome above the normative values for clinically stable post-transplantation patients but below a predetermined threshold level could indicate a less serious condition such as a viral infection rather than transplant rejection. An increase in the amount of one or more nucleic acids from the microbiome above a higher threshold could indicate transplant rejection.

In some embodiments, temporal differences in the amount of said one or more nucleic acids from the microbiome are indicative of immunocompetence. For instance, a transplant patient can be monitored over time to determine the amount of one or more nucleic acids from the microbiome. A temporary decrease in the amount of one or more nucleic acids from the microbiome, which subsequently return to normal values, might indicate a less serious condition rather than transplant rejection. On the other hand, a sustained decrease in the amount one or more nucleic acids from the microbiome might indicate a serious condition such as lack of effective immunosuppression and graft rejection.

In some embodiments, temporal differences in the amount of said one or more nucleic acids from the microbiome can be used to monitor effectiveness of an immunosuppressant treatment or to select an immunosuppressant treatment. For instance, the amount of one or more nucleic acids from the microbiome can be determined before and after an immunosuppressant treatment. A decrease in the one or more nucleic acids from the microbiome after treatment may indicate that the treatment was successful in preventing transplant rejection. Additionally, the amount of one or more nucleic acids from the microbiome can be used to choose between immunosuppressant treatments, for examples, immunosuppressant treatments of different strengths. For example, a lower amount in one or more nucleic acids from the microbiome may indicate that there is a need of a very potent immunosuppressant, whereas a higher amount in one or more nucleic acids from the microbiome may indicate that a less potent immunosuppressant may be used.

The invention provides methods that sensitive and specific. In some embodiments, the methods described herein for diagnosing or predicting transplant status or outcome have at least 56%, 60%, 70%, 80%, 90%, 95% or 100% sensitivity. In some embodiments, the methods described herein have at least 56% sensitivity. In some embodiments, the methods described herein have at least 78% sensitivity.

In some embodiments, the methods described herein have a specificity of about 70% to about 100%. In some embodiments, the methods described herein have a specificity of about 80% to about 100%. In some embodiments, the methods described herein have a specificity of about 90% to about 100%. In some embodiments, the methods described herein have a specificity of about 100%.

The invention provides non-invasive diagnostics for individuals, including individuals that are being treated with immunosuppressive regimens, treated with anti-microbial agents, etc., by monitoring the sequences of cell-free DNA or RNA from non-human sources. For example, individuals carry a number of virus, where the virus load is shown herein to vary with the immunocompetence of the individual. Preferred virus for monitoring immunocompetence are annellovirus, in which the viral burden is shown herein to correlate with immunocompetence of the individual.

In some embodiments, the invention provides methods, devices, compositions and kits for detection and/or quantitating circulating nucleic acids, usually free in plasma or from viral particles, for the diagnosis, prognosis, detection and/or treatment of an infection, of immunocompetence, transplant status or outcome.

In some specific embodiments, the invention provides an approach to noninvasive detection of immunocompetence in transplant patients by virome analysis, which circumvents the potential problems of microchimerism from DNA from other foreign sources and is general for all organ recipients without consideration of gender. In some embodiments, a genetic fingerprint is generated for the virome of the individual. This approach allows for a reliable identification of sequences that can be made in a manner that is independent of the genders of donor and recipient.

Following an immunosuppressive regimen, e.g. in conjunction with transplantation, treatment of autoimmune disease, etc., bodily fluid such as blood can be drawn from the patient and analyzed for markers. Examples of bodily fluids include, but are not limited to, smears, sputum, biopsies, secretions, cerebrospinal fluid, bile, blood, lymph fluid, saliva, and urine. Detection, identification and/or quantitation of the virome sequences can be performed using real-time PCR, chips, high-throughput shotgun sequencing of circulating nucleic acids (e.g. cell-free DNA), as well as other methods known in the art including the methods described herein. The viral load can be monitored over time and an increase in this proportion can be used to determine immunocompetence status or outcome.

In any of the embodiments described herein, the transplant graft can be any solid organ or skin transplant. Examples of organ transplants that can be analyzed by the methods described herein include but are not limited to kidney transplant, pancreas transplant, liver transplant, heart transplant, lung transplant, intestine transplant, pancreas after kidney transplant, and simultaneous pancreas-kidney transplant.

In some other embodiments, the methods of the invention are used in determining the efficacy of a therapy for treatment of disease, including infection, either at an individual level, or in the analysis of a group of patients, e.g. in a clinical trial format. Such embodiments typically involve the comparison of two time points for a patient or group of patients. The patient status is expected to differ between the two time points as the result of a therapeutic agent, therapeutic regimen, or disease challenge to a patient undergoing treatment.

Examples of formats for such embodiments may include, without limitation, analyzing the microbiome at two or more time points, where a first time point is a diagnosed but untreated patient; and a second or additional time point(s) is a patient treated with a candidate therapeutic agent or regimen.

In another format, a first time point is a diagnosed patient in disease remission, e.g. as ascertained by current clinical criteria, as a result of a candidate therapeutic agent or regimen. A second or additional time point(s) is a patient treated with a candidate therapeutic agent or regimen, and challenged with a disease-inducing agent, for example in a vaccine context.

In such clinical trial formats, each set of time points may correspond to a single patient, to a patient group, e.g. a cohort group, or to a mixture of individual and group data. Additional control data may also be included in such clinical trial formats, e.g. a placebo group, a disease-free group, and the like, as are known in the art. Formats of interest include crossover studies, randomized, double-blind, placebo-controlled, parallel group trial is also capable of testing drug efficacy, and the like. See, for example, Clinical Trials: A Methodologic Perspective Second Edition, S. Piantadosi, Wiley-Interscience; 2005, ISBN-13: 978-0471727811; and Design and Analysis of Clinical Trials: Concepts and Methodologies, S. Chow and J. Liu, Wiley-Interscience; 2003; ISBN-13: 978-0471249856, each herein specifically incorporated by reference.

Examples

Temporal Response of the Human Virome to Immunosuppression and Antiviral Therapy The viral component of the microbiome, the human virome, remains relatively understudied (Wylie et al. (2012) Transl Res 160, 283-290) and little is known about the effects of immune modulation and antiviral therapies on virome composition. It was previously shown that the healthy gut virome remains remarkably stable over time (Reyes et al. (2010) Nature 466, 334-338), and that the predominant source of variation is due to differences between subjects, although an association between diet and the virome composition was found (Minot, et al. (2011). Genome Research 21, 1616-1625).

Immunosuppressive therapies significantly reduce the risk of graft rejection in organ transplantation but increase the susceptibility of recipients to infections. Infections with viral pathogens, in particular the herpesvirus cytomegalovirus (CMV), occur frequently and increase the recipient's risk of graft failure. Organ transplant recipients are therefore frequently subjected to antiviral prophylactic or preemptive therapies directed against CMV.

The inverse relationship between the level of immunosuppression and the risks of infection and rejection leaves only a narrow therapeutic window available for patient treatment. Post-transplant care is further complicated by numerous limitations of the currently available methods for the diagnosis of infection and rejection. Diagnosis of rejection mostly relies on invasive biopsies that suffer from interobserver variability, high cost and patient discomfort. Diagnosis of infections is challenging given the fact that the symptoms of infection are diminished following immunosuppression, and commonly used diagnostic methods, such as antigen-detection and PCR-based molecular tests, rely on a specific target and therefore an a priori hypothesis for the source of the infection.

As a final complication, patient-to-patient variability in the sensitivity to immunosuppressive drugs can give rise to over- and under immunosuppression, increasing the risk of infection or rejection respectively.

There are few substantive methods to measure the health of the immune system, and the connection between immunocompetence and the viral component of the microbiome is poorly understood. Organ transplant recipients are treated with a post-transplant therapy that combines immunosuppressive and antiviral drugs, offering a window into the effects of immune modulation on the human virome. We used sequencing of cell-free DNA in plasma to investigate drug-virome interactions in a cohort of organ transplant recipients (656 samples, 96 patients), and find that antivirals and immunosuppressants strongly affect the structure of the virome in plasma. We observe marked virome compositional dynamics at the onset of the therapy and find that the total viral load increases with immunosuppression, whereas the bacterial component of the microbiome remains largely unaffected. The data provide insight into the relationship between the human virome, the state of the immune system, and the effects of pharmacological treatment, and offer a potential application of the virome state to predict immunocompetence.

In this work, we sequenced cell-free DNA circulating in plasma to investigate drug-microbiome interactions following organ transplantation. We studied the patterns of infection in heart and lung transplant recipients subjected to a combination of immunosuppressants and antiviral prophylaxis. We find that immunosuppressants and antivirals have a strong influence on the structure of the viral component of the microbiome but not the bacterial component. Strong compositional dynamics are observed at the onset of the drug therapy as the virome composition of different individuals converge to a similar, drug-determined state. The total viral load increases markedly in response to the therapy, as viruses, in particular the anelloviruses, take advantage of a reduction of immunocompetence. Finally, we show that measurement of the anellovirus burden enables stratification of rejecting and non-rejecting recipients.

656 plasma samples were collected longitudinally from 96 solid organ transplant recipients (41 adult heart, 24 pediatric heart, 31 adult lung). Cell-free DNA was purified from plasma and sequenced. In total, we obtained 820 gigabases (Gbp) of sequencing data, with an average of 1.25 Gbp per sample (Illumina HiSeq, 1×50 bp reads, FIG. 1B). Organ transplant recipients were continuously enrolled in the study over the course of more than 2 years and samples were collected from the recipients at regular time points post transplant, with the highest frequency of sample collection in the first months post transplant. FIG. 1C shows the number of samples analyzed as a function of time post transplant for the different patient classes.

The patients in the cohort were treated with antiviral prophylaxis and immunosuppression as part of a standardized post-transplant therapy (FIG. 1D). Maintenance immunosuppression was tacrolimus-based for the adult heart and lung transplant recipients and was complemented with mycophenolate mofetil and prednisone. Pediatric patients were treated with a cyclosporine based anti-rejection therapy. CMV positive transplant recipients (prior CMV infection for recipient and/or donor), but not CMV negative recipients, were treated with antiviral prophylaxis. The protocol design entails high doses of immunosuppressants and antiviral drugs in the first few months post transplant, after which the doses are gradually reduced as the risks of rejection and infection diminish. Given the narrow therapeutic window available for immunosuppression and the large patient-to-patient variability in pharmacokinetics of tacrolimus, the concentration of the tacrolimus is directly measured in the blood and the dose is adjusted to maintain a target drug level. FIG. 1D shows the mean level of tacrolimus measured in blood for the tacrolimus-treated patients and illustrates the design of the drug treatment protocol.

DNA sequence analysis. Microbiome-derived sequences were identified after computational subtraction of human-derived sequences. To this end, duplicate and low quality reads were removed and the remaining reads were mapped to the human reference genome, build hg19 (BWA (Li and Durbin, 2009), see methods). Unmapped reads were then collected and low complexity reads were removed. FIG. 1E shows the distribution of the remaining read fraction after applying duplicate and quality filters (average of 86%) and the distribution of the remaining fraction after subtraction of human reads (average of 2%).

Figure 6:
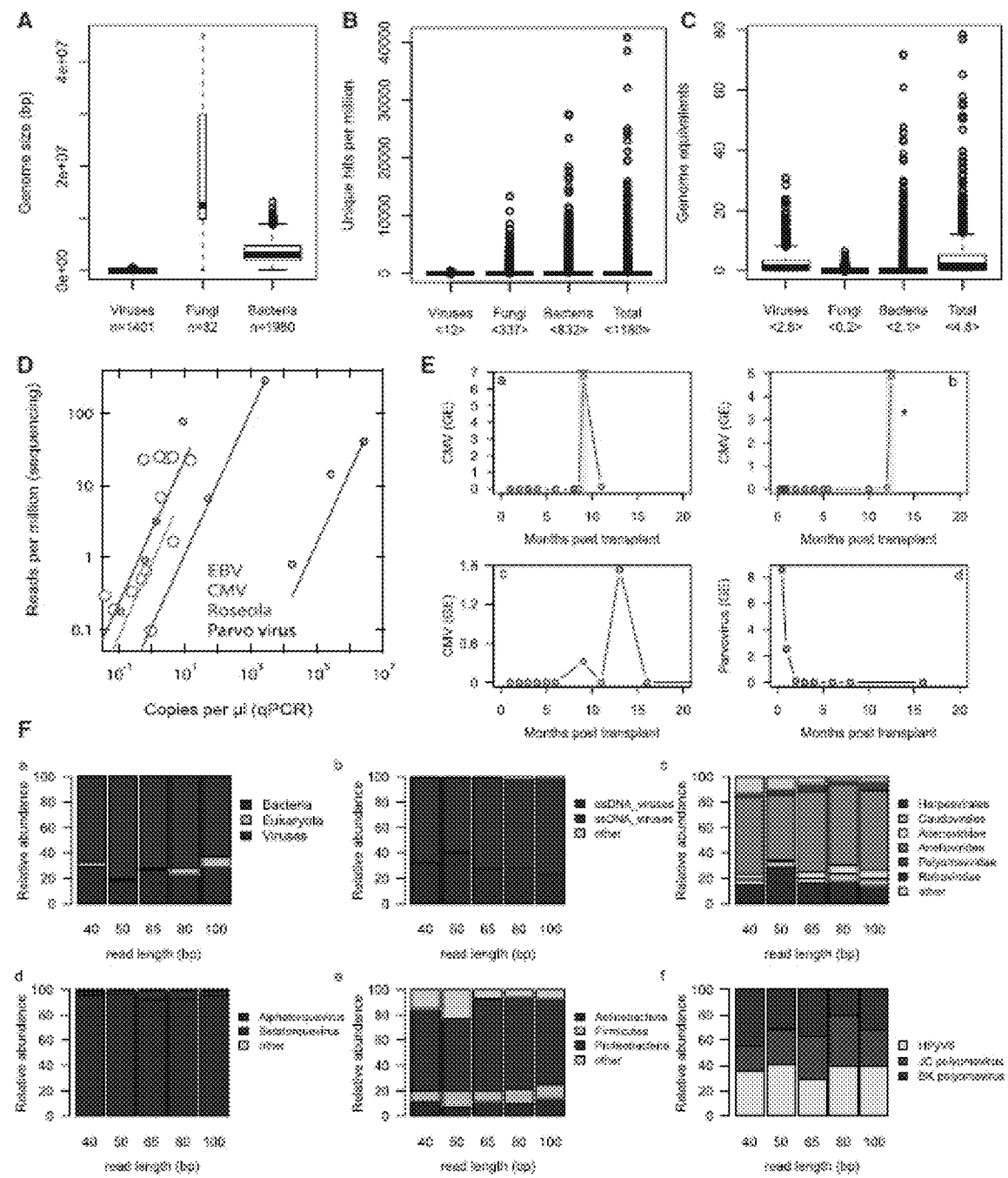
FIG. 6. Genome Sizes and Hit Statistics, qPCR Assay and Influence of Read Length on Measured Relative Abundance of Species at Different Levels of Taxonomic Classification (A) Distribution of genome sizes in the reference database with, 1401 viral genomes, 32 fungal genomes and 1980 bacterial genomes. (B) Distribution of unique blast hits per million unique molecules sequenced (average number of hits specified in the x axis label). C. Distribution of genome equivalents (infectious agents/diploid human) for viruses, bacteria and fungi (average number of genome equivalents specified in the x axis label). (D) Comparison of sequencing hits found per million of total reads sequenced to the number of viral copies detected using qPCR. For the qPCR assays, DNA was purified from 1 ml of plasma and eluted in a 100 µl volume. (E) Measurements of CMV and parvovirus burdens for selected cases. The highest loads of CMV virus (genome equivalents, viral/human diploid, G. E.) measured for all samples corresponded to two cases of clinically diagnosed disseminated CMV infection (a and b, shaded area denotes time-window of clinical diagnosis, * denotes time of death). (c) shows a time trace of a pediatric patient that suffered from CMV viremia. Parvovirus was detected in one pediatric heart transplant patient immediately post-transplant (d).* (F) Influence of read length on measured relative abundance of species at different levels of taxonomic classification (n=52). Spearman sample-to-sample correlation, r, and p value, p, (two-sample Mann-Whitney U test) for the abundance of the most abundant node extracted from the 50 and 100 bp data sets: r=0.80, p=0.8 (a), r=0.86, p=0.4 (b), r=0.92, p=0.6 (c), r=0.84, p=0.5 (d), r=0.7, p=0.28 (e), r=0.99, p=1 (f).

To identify infectious agents, the remaining, high quality, unique, non-human reads were mapped using BLAST to a reference database of viral (n=1401), bacterial (n=1980) and fungal (n=32) genomes (downloaded from NCBI, FIG. 6A). 0.12% of the uniquely sequenced reads aligned to at least one of the target genomes (FIG. 6B, C). We used a quantitative PCR (qPCR) assay targeted to a subset of sequencing identified targets (herpesviruses 4,5,6 and parvovirus) to validate the positive hits identified by the sequencing-based approach. We found a quantitative agreement between viral counts as measured by sequencing and qPCR (FIG. 6D).

We furthermore found that the sensitivity of the sequencing assay for the detection of herpesviruses is on par with qPCR measurements. The larger capture cross-section available to the sequencing assay—the complete target genome versus the PCR amplicon target region—is thus sufficient to overcome the signal loss in sequencing, caused by the finite efficiency of sequencing library preparation and library undersampling. The highest CMV loads measured using sequencing across all samples in the study corresponded to two adult heart transplant patients that suffered from a clinically diagnosed disseminated CMV infection (see FIG. 6E).

To test for the presence of potential contaminants in the reagents used for DNA extraction and sequencing library preparation, we performed two control experiments. In the first, we prepared 2 samples with a known template (Lambda gDNA, Pacbio Part no: 001-119-535), and purified DNA for sequencing using the above-described workflow (Illumina Miseq, 3.4 and 3.5 million reads). Lambda-derived sequences were removed and the remaining sequences (0.4%) were aligned to the BLAST reference database described above. No evidence was found for the various infectious agents discussed in this work, but we did detect sequences related to the Enterobacteriaceae bacterial family (phylum Proteobacteria), primarily *E. coli* (>97%), and enterobacterial phages (<1%), which are likely a remnant of the lambda DNA culture. In a second control, we prepared a sample for sequencing from nuclease-free water. The sample was included in a sequencing run along with a sample unrelated to this work and recruited only a limited number of sequences, 15 in total, which mapped to genomes of two bacterial species. Again, no evidence was found for the infectious agents that are discussed below.

We studied the microbiome composition in plasma at different levels of taxonomic classification using Grammy, a tool that utilizes the sequence-similarity data obtained with BLAST to perform a maximum likelihood estimation of the relative abundance of species. GRAMMy accounts for differences in target genome size and the ambiguity of read assignments. Note that this approach only allows estimating the abundance of species for which genomic data is available in the reference database. FIG. 1F shows the relative abundance of species at different levels of taxonomic classification (average over all samples). We find that viruses (73%) are more abundantly represented than bacteria (25%) and fungi (2%) (FIG. 1F panel a). Among viruses, we find that ssDNA viruses occupy a larger fraction (72%) than dsDNA viruses (28%). Seven distinct viral families are found (abundance>0.75%), with one dominant family, the Anelloviridae, which accounted for 68% of the total population (FIG. 1F, panel b). The anelloviridae fraction is mostly (97%) composed of viruses from the Alphatorquevirus genus (FIG. 1F, panel c). The Alphatorque genus is the genus of Torque Teno Viruses (TTVs), and sequences related to 14 different torque teno virotypes were identified (FIG. 1, panel d). Infections with polyomaviruses are widespread in the human population, and polyomavirus DNAemia is not uncommon in the first year after solid organ transplantation. Polyomavirus-derived sequences were found in 75 samples (11%) corresponding to 36 patients in the present cohort. Evidence for the presence of BK (41%), JC (27%), TS (4%), WU polyomavirus (6%), SV40 (6%) and the recently discovered HPyV6 (13%) (Schowalter et al., 2010) was found (FIG. 1F, panel e). Among bacteria, Proteobacteria (36%), Firmicutes (50%), Actinobacteria (10%), Bacteroidetes (4%) are the phyla most abundantly represented in the sample (FIG. 1F, panel f).

To investigate potential incorrect assignments of the relatively short reads available to this study (50 bp), we examined the dependence of the abundance estimates on read length, based on longer, paired-end reads (2×100 bp) collected for a subset of samples (n=55). We found that the abundance estimates based on 50 bp subreads and 100 bp reads are similar for all levels of taxonomic classification reported here (FIG. 6F).

Sensitivity of virome composition to drug dosage. The available clinical data on drug dosage was used to analyze drug-microbiome interactions. Here, we examined data for the adult heart and lung transplant patients that were treated with a tacrolimus-based anti-rejection protocol (47 patients and 380 observations), thereby excluding the pediatric patients that were treated with cyclosporine and patients that were switched from tacrolimus to cyclosporine immunosuppression due to drug-intolerance issues. Data on prescription antiviral drug doses (valganciclovir) and the measured levels of tacrolimus in blood were collected from individual patient records and the mean composition for samples corresponding to different drugs levels was extracted. To account for a delayed effect of the microbiome composition on dose changes, the drug level and dose data were sliding window average filtered (see FIG. 1C and FIG. 7A-C; window size 45 days).

Figure 2:
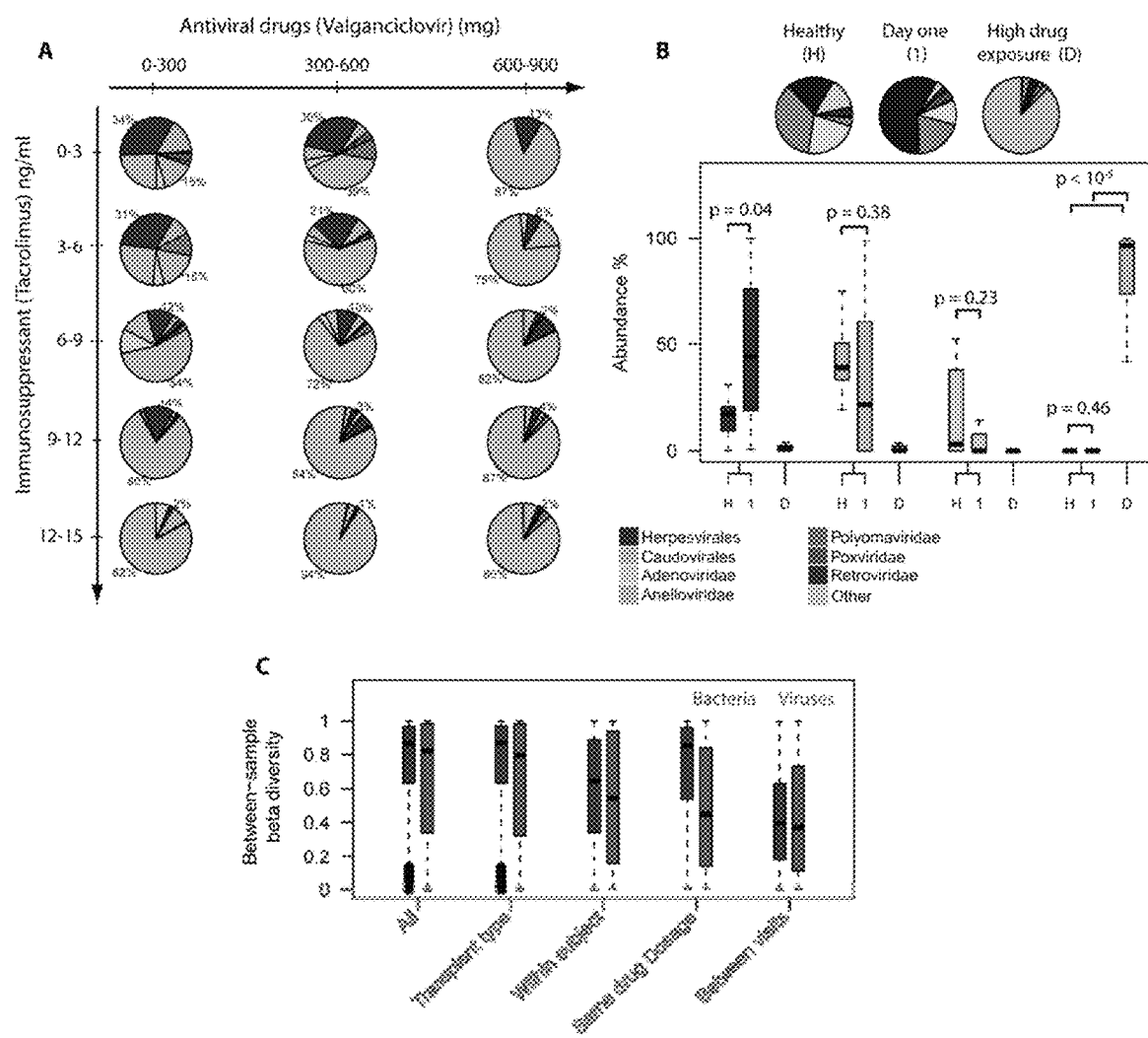
FIG. 2. Relative viral genomic abundance as a function of drug dose and comparison to healthy reference. A. Mean virome composition for patients treated with the immunosuppressant tacrolimus (47 patients, 380 samples) as function of antiviral drug dose (valganciclovir) and concentration tacrolimus measured in blood. To account for the delayed effect of the virome composition on drug dose, the data on drug doses were window average filtered (window size 45 days, see FIG. 1C). Herpesvirales and caudovirales dominate the virome when patients receive low doses of immunosuppressants and antiviral drugs. Conversely, anelloviridae dominate the virome when patients receive high doses of these drugs. B. Comparison of virome composition corresponding to healthy references (n=9), post-transplant day one samples with low drug exposure, (n=13), and samples corresponding to high drug exposure (tacrolimus 9 ng/ml, valganciclovir 600 mg, n=68). The virome structure for day one samples (1) and the virome structure measured for a set of healthy individuals (H) are distinct from the anellovirus-dominated distribution measured for samples corresponding to high drug doses (D). The piecharts show the mean fractions, p-values in boxplot based on the Mann-Whitney test. C. Bray-Curtis beta diversity for all samples, among patients with the same transplant type (heart or lung), within subjects, for patients treated with a similar drug dosage (tacrolimus level±0.5 ng/ml, valganciclovir±50 mg), and for samples collected from the same subjects within a one-month timespan.
Figure 7:
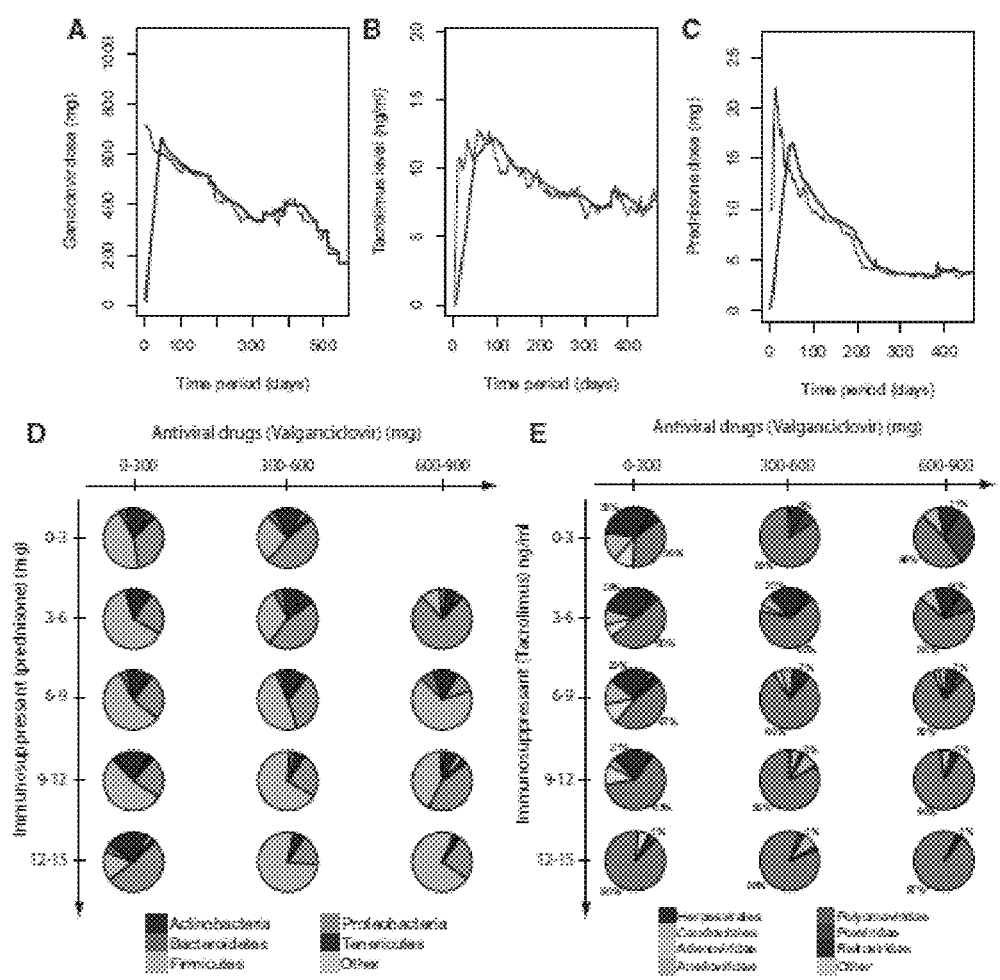
FIG. 7. Average Drug Doses and Measured Levels for Adult Heart and Lung Transplant Patients after Transplantation and Influence of Drug Dosage on Virome composition. (A-C) Average dose of valganciclovir and prednisone (A and C) administered and measured level of tacrolimus in blood (B) for the adult heart and lung transplant patients part of this study. (D) Compared to the viral component, the composition of the bacterial component of the microbiome is relatively insensitive to antivirals and immunosuppressants. (E) Virome composition as function of dose of anti-CMV drug (valganciclovir) and immunosuppressant (prednisone).

We find that the structure of the viral component of the microbiome is a sensitive function of drug dosage (47 patients, 380 samples, FIG. 2A). However, the structure of the bacterial component of the microbiome was not significantly altered by the drug therapy, as discussed further below (FIG. 7D). Herpesvirales and caudovirales dominated the virome when patients received a low dose of valganciclovir and tacrolimus. In contrast, a high dose of immunosuppressants and antivirals gave rise to a virome structure that is dominated by anelloviridae (up to 94% occupation at high drug levels). The antiviral prophylaxis is intended to prevent CMV disease, but other herpesviruses are also susceptible to the drug so it is not surprising that a higher dose of valganciclovir gives rise to a lower fraction of viruses from the Herpesvirales order. The observation that anelloviridae take advantage of suppression of the host immune system is consistent with various observations from the literature: it was previously shown that the incidence of anelloviridae increases with progression towards AIDS in HIV patients, and that the total burden of the anellovirus TTV increases post liver transplantation. Furthermore, an increased prevalence of anelloviridae in pediatric patients with fevers was reported recently.

We next compare the virome composition measured for organ transplant recipients to the composition observed in healthy individuals, not on immunosupressants or antivirals (n=9, sequencing data available from a previous study). Here, we compare the healthy composition to the composition measured for organ transplant recipients at the start of the drug therapy (postoperative day one, n=13), corresponding to a minimal drug exposure, and to the composition measured for transplant recipients exposed to high drug levels (well after the transplant procedure, tacrolimus 9 ng/ml. valgancicolvir 600 mg, n=68). We find a similar composition of the virome for the healthy reference samples and samples corresponding to minimal drug exposure (FIG. 2B). However, the compositions of the healthy reference and minimal drug exposure samples are distinct from the anelloviridae-dominated composition measured for high drug exposure samples.

The tacrolimus-based immunosuppressive therapy is complemented with induction therapy in the first 3 days post transplant (with anti-thymocyte globulin, daclizumab, or basiliximab) and the patients furthermore receive the corticosteroid prednisone throughout the post transplant therapy. The time-dosage profile for prednisone and tacrolimus are similar: high doses at the onset of the therapy followed by a gradual dose reduction (FIG. 7A-C). The data in FIG. 2A thus reflect the combined effect of prednisone and tacrolimus. An analysis of the differential effect of prednisone and valganciclovir on the virome composition (FIG. 7E) shows the same trend observed in FIG. 2A: higher prednisone doses lead to a larger representation of anelloviruses. Lastly, we note that a subset of patients was not treated with antiviral drugs. The data corresponding to this subset of patients allowed us to further disentangle the differential effect of the antiviral drugs and the immunosuppressants on the composition of the virome, as described below.

Partitioning of microbiome diversity. We studied the diversity of the bacterial and viral components of the microbiome. The within-subject diversity was lower than the between-subject diversity, both for bacteria and viruses (Bray-Curtis beta diversity, bacterial composition at phylum level, family and order level viruses, FIG. 2C). Partitioning the data for patients according to transplant type, heart or lung, or age did not reduce the diversity. Within subjects, the diversity was lower for samples collected within a one month timespan, again both for bacteria and viruses. For viruses but not for bacteria, we find that the diversity is lower when comparing samples collected at a similar drug dosage (tacrolimus level±0.5 ng/ml, valganciclovir±50 mg). Taken together with the sensitivity of the population averages to drug dosage in FIG. 2A, we thus find that the composition of the virome for patients that are subject to the same drug therapy converges to a similar state.

Figure 3:
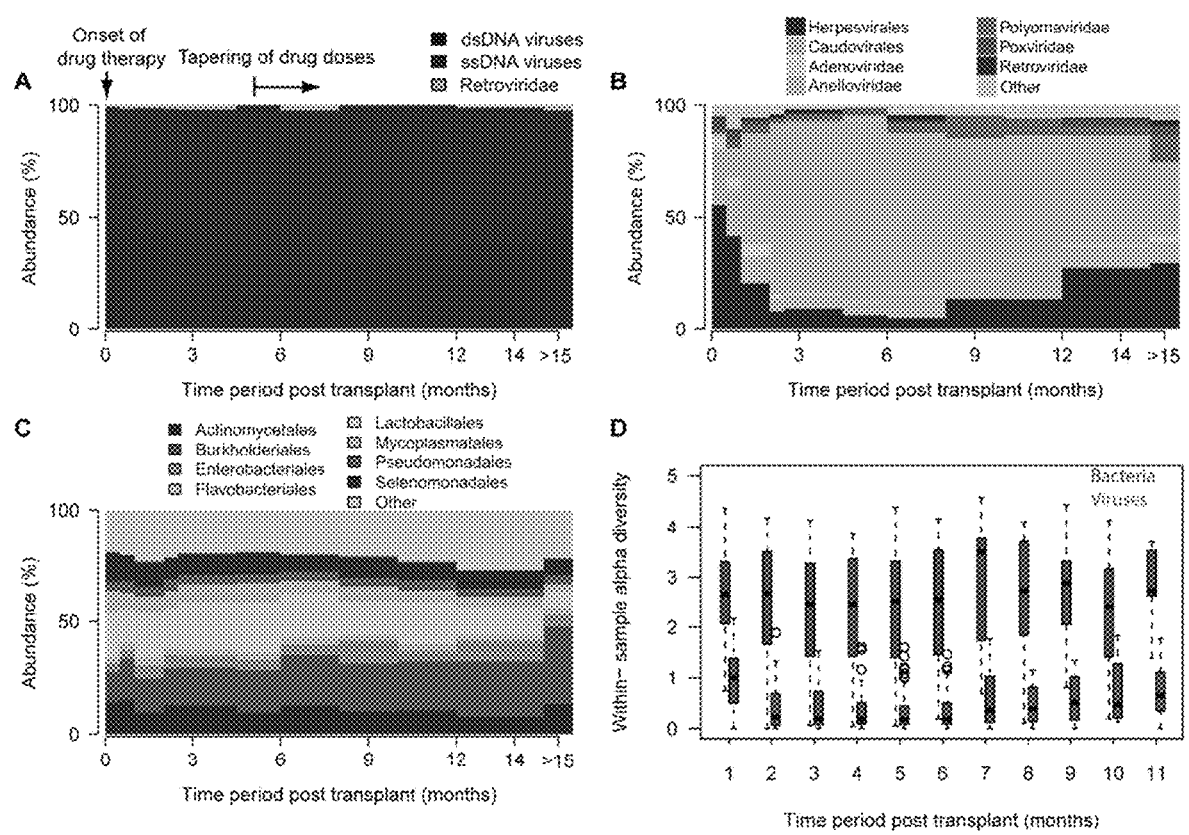
FIG. 3. Temporal dynamics of the microbiome composition post-transplant. A. Relative abundance of dsDNA and ssDNA viruses for different time periods (average for all samples). The relative abundance of ssDNA viruses increases rapidly after the onset of the post-transplant drug therapy. After 6 months, the opposite trend is observed. B. Viral genome abundance at the family and order level of taxonomic classification for different time periods. The fraction of anelloviridae expands rapidly in the first several months post-transplant. The fraction of herpesvirales, caudovirales and adenoviridae decreases in that same time period. After 6 months, the opposite trends are observed. C. Time-variation in the relative abundance of bacterial phyla. Compared to the viral abundance, the representation of different bacterial phyla is relatively unchanged over the observed post-transplant period. D. Shannon entropy as a measure of the within-sample alpha-diversity for bacterial and viral genera as function of time (data grouped per one month time period).

Dynamic response of virome to drug dose changes. A strong temporal response of the virome to changes in drug dosage is observed, consistent with the sensitivity of the virome composition to drug dosage. FIG. 3A shows the time dependence of the relative genomic abundance of ssDNA and dsDNA viruses (data from all patient groups and samples, n=656). The fraction of ssDNA viruses expands rapidly during the first months post transplant followed by the opposite trend after 6 months. FIG. 3B shows the time-dependent relative composition of the most abundant viruses grouped at the family and order level and provides more detail on the virome compositional dynamics (data from all patient groups and samples, n=656). The dsDNA fraction consists of caudovirales, adenoviridae, polyomaviridae and herpesvirales, which together occupy 95% of the virome in the first week(s) post transplant. ssDNA viruses only occupy 5% of the initial virome and mainly consist of members of the anelloviridae family. The fraction occupied by adenoviridae, caudovirales and herpesvirales decreases strongly in the first few months as these virotypes are effectively targeted by the antiviral prophylaxis. In contrast, the relative abundance of anelloviridae increases rapidly as these virotypes largely escape targeting by the antiviral drugs and take advantage of the reduced immunocompetence of the patients (maximum of 84% during months 4.5-6). Six months after the organ transplant procedure, the opposite trends are observed, consistent with the reduction in antiviral and immunosuppressant drugs prescribed by the therapeutic protocol.

Compared to the viral component, the bacterial component of the microbiome remains relatively stable over time, an observation that is made at the phylum, order and genus taxonomic levels (FIG. 3C, n=656, and FIG. S3). FIG. 3D shows the within-sample alpha diversity for the bacterial and viral genera as function of time (Shannon entropy, one month time periods, 590 bacterial genera, 168 viral genera examined). The diversity of observed viral genera decreases at the onset of the therapy ($1.05\pm0.5$ in month 1 to $0.31\pm0.33$ in months 4-5, $p\ll10^{-6}$, Mann-Whitney U test), whereas the alpha diversity of bacteria remains relatively unchanged during the course of the post transplant therapy ($2.2\pm1.14$ in month 1 to $2.6\pm0.85$ in months 4-5, $p=0.1$, Mann-Whitney U test).

Figure 4:
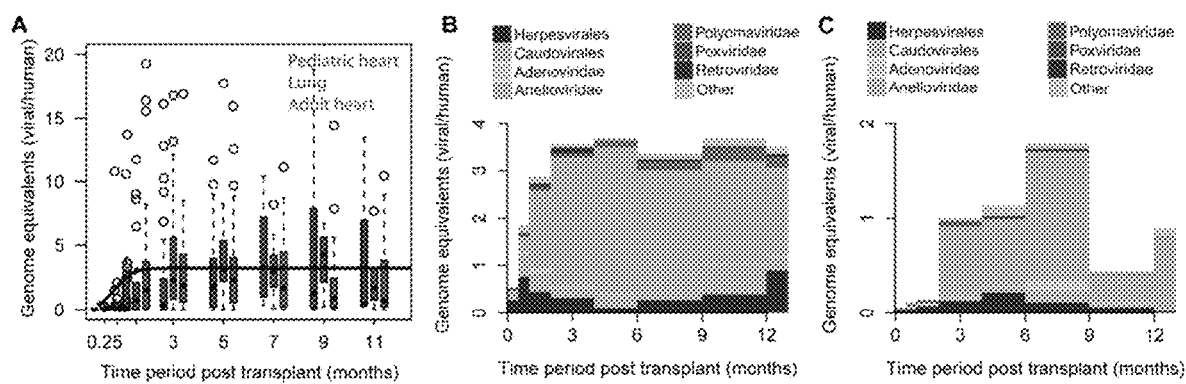
FIG. 4. Virome composition and total viral burden in the absence and presence of antiviral prophylaxis. A. Absolute viral load as a function of time, measured as viral genome copies per human genome copies detected by sequencing. Box plots are shown for different time periods with centers of the time periods marked on the x-axis. For all patient classes, the total viral load increases in the first weeks post-transplant (black line is sigmoid fit, change in load 7.4±3). B. Viral load and composition for CMV+ cases that are treated with both immunosuppressants and antiviral drugs (78 patients, 543 samples). C. Viral load and composition for CMV−/− cases, only treated with immunosuppressants (12 patients, 75 samples).

Increase in total viral load at onset of post transplant therapy. To obtain insight into the effect of therapeutic drugs on total viral load, we extracted the absolute genomic abundance of all viruses relative to the number of human genome copies by normalizing the genome coverage of the viral targets to the coverage of the human genome. For all patient groups part of this study an increase in total viral load is observed at the onset of the therapy (FIG. 4A), regardless of transplant type (heart or lung) or age (adult or pediatric) (change in load, $7.4\pm3$, sigmoid fit, black line). Combined with relative abundance data, the total viral load data reveals a net reduction of the Herpesvirales load and a net increase in anelloviridae load in the first 3 months post-transplant for patients that are simultaneously treated with antivirals and immunosuppressants.

Figure 8:
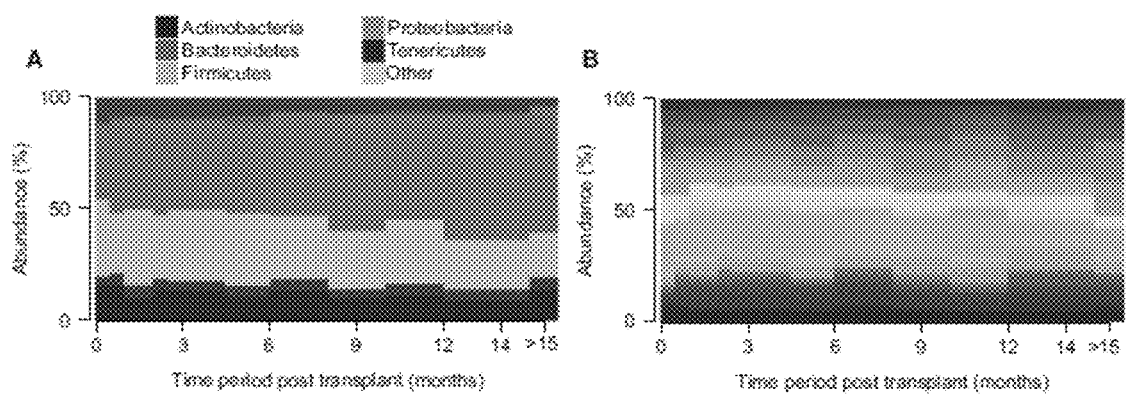
FIG. 8. Temporal Dynamics of the Bacterial Component of the Microbiome Posttransplant, (A) Relative abundance of bacterial phyla as function of time. (B) Relative abundance of bacterial genera as function of time.

The data thus show a differential effect of the combination of antivirals and immunosuppressants on different virotypes. The data also show a reduction in total adenoviridae load, indicating that adenoviridae replication is suppressed by valganciclovir, in agreement with previous studies. FIG. 4B summarizes data for all transplant types, but the same trends are observed when stratifying according to different transplant types: adult heart transplant recipients (n=268, FIG. 9A), adult lung transplant recipients (n=166, FIG. 8B), and the pediatric patients that are treated with cyclosporine as opposed to tacrolimus (n=99, FIG. 9C).

Figure 9:
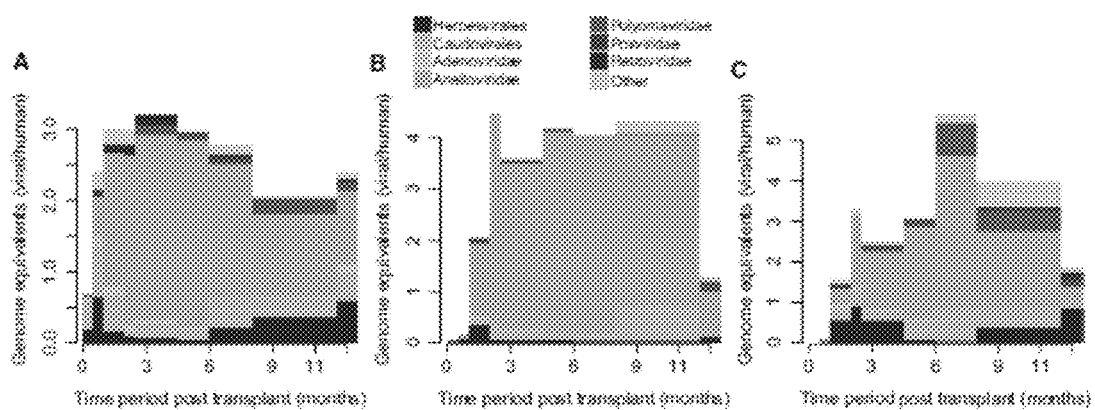
FIG. 9. Virome Composition and Total Viral Burden for Different Patient Classes, (A and B) Viral load and composition for CMV positive adult heart (A), adult lung (B), and pediatric heart (C) transplant recipients, treated with both immunosuppressants and antivirals.

Not all patients in the study cohort received both antiviral and immunosuppressant drugs: for transplant cases where both the donor and recipient do not show evidence of a prior CMV infection in a CMV antibody assay, it is judged that the risks of complications due to antiviral prophylaxis outweigh the potential risk of a newly acquired CMV infection, and the patients are accordingly not treated with antiviral prophylaxis. These patients are thus solely treated with immunosuppressants. FIG. 9C shows the time dependent viral load and composition of the CMV negative cases (n=75). The net effect of immunosuppressant-only therapy is an expansion of all virotypes, including Herpesvirales and adenoviridae. Tapering of immunosuppression leads to a reduction of the total viral load.

Figure 5:
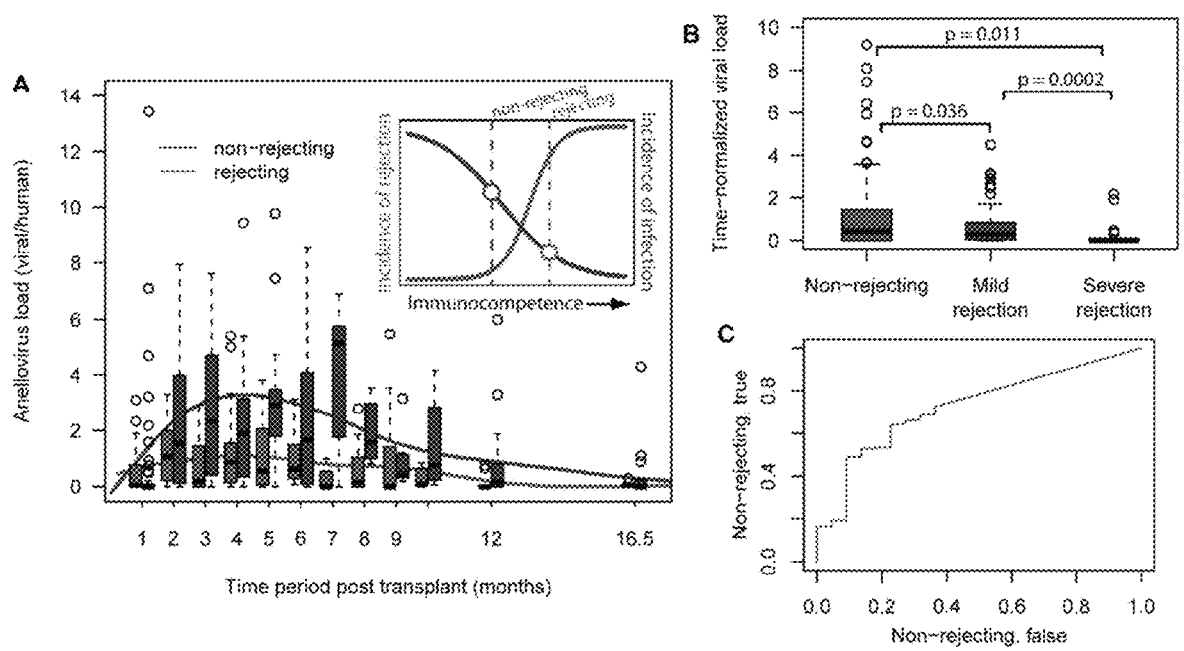
FIG. 5. Lower anellovirus burden in patients that suffer from graft rejection. A. Time dependence of the anellovirus load in the subgroup of patients that suffer from a severe rejection episode (biopsy grade ≥2R/3A, red data, 20 patients, 177 time points) and in the subgroup of patients that do not suffer from a severe-rejection-free post-transplant course (blue data, 40 patients, 285 time points). Box plots are shown for different time periods with centers of the time periods marked on the x-axis. Solid lines are cubic splines (smoothing parameter 0.75). The inset shows a cartoon of the expected opposite association of the incidence of rejection and infection with immunocompetence. B. Anellovirus load relative to the average load measured for all samples at the same time point. The time-normalized load for non-rejecting patients (N=208) is compared to the load measured for patients suffering from a mild rejection event (biopsy grade 1R, N=102) and patients suffering from a severe rejection episode (biopsy grade ≥2R/3A, N=22). The p-values reflect the probability that the median viral load is higher for the subgroups at greater risk of rejection. The p-values are calculated by random sampling of the population with a greater amount of measurement points. N-fold random sampling, $p=\text{sum}(\text{median}(A_{rej})>\text{median}(A_{non-rej}))/N$, where $N=10^4$ and $A_{rej}$ and $A_{non-rej}$ are the relative viral loads for the populations at greater and lesser risk of rejection and non-rejecting respectively. C Test of the performance of the relative anellovirus load in classifying patients as non-rejecting vs. severely rejecting, receiver-operating characteristic curve, area under the curve=0.72.

Lower anellovirus burden in patients suffering from a graft rejection episode. Given the correlation of the anellovirus burden with the extent of immunosuppression (see FIG. 2A and FIG. 4), and given the association between immunocompetence and the risk of rejection, we asked whether the anellovirus burden can be used for the classification of rejecting and non-rejecting graft recipients. FIG. 5A shows the anellovirus load measured for rejecting and non-rejecting patients as function of time post transplant. Here, patients are classified as rejecting in case they suffer from at least one biopsy-determined moderate or severe rejection episode, biopsy grade ≥2R/3A (in red; 20 patients, 177 data points). The rejection-free patients correspond to patients that are not diagnosed to suffer from a moderate or severe graft damage throughout their post transplant course (in blue; biopsy grades <2R/3A, 40 patients, 285 data points).

FIG. 5A shows that the anellovirus burden is significantly lower for the rejecting individuals at almost every time point. We next directly compared the anellovirus burden for patients at rejection with the burden measured for patients in the absence of rejection. To account for the time dependence of the anellovirus load described above (FIG. 5A), we extract the anellovirus load relative to the mean load measured for all samples at the same time point. FIG. 5B shows the time-normalized load for non-rejecting patients (N=208) compared to the load measured for patients suffering from a mild rejection event (biopsy grade 1R, N=102) and patients suffering from a severe rejection episode (biopsy grade ≥2R/3A, N=22). The figure shows that the time-normalized loads are significantly lower for the patients at greater risk of rejection. P-values were calculated by random sampling of the population with a greater amount of measurement points, $p=\text{sum}(\text{median}(A_{rej})>\text{median}(A_{non\_rej}))/N$, where $N=10^4$ and $A_{rej}$ and $A_{non-rej}$ are the relative viral loads for the populations at greater and lesser risk of rejection and non-rejecting respectively (p=0.011, p=0.0002 and p=0.036).

These observations are in line with a view that the risk of rejection and the incidence of infection have an opposite association with the patients' immunocompetence (see inset FIG. 5A). The lower viral load observed for rejecting patients is thus indicative of a higher level of immunocompetence in this subgroup of patients, even though these patients are treated with the same immunosuppressive protocol. Patient-to-patient variability in the sensitivity to suppression of immune function is known to occur and the lack of predictability in immunosuppression is an important risk factor in transplantation. A presently-used commercial assay for the measurement of immunocompetence has not been found to be predictive of acute rejection or significant infections. The development of methods for the direct measurement of immunocompetence, that can replace or complement existing assays, will therefore be important. The total anellovirus load recorded in organ transplant recipients could serve as an alternative marker. FIG. 5C shows a receiver-operating characteristic and tests the performance of the relative anellovirus load in classifying non-rejecting and rejecting patients (area under the curve=0.72).

We have studied drug-microbiome interactions following solid organ transplantation by sequencing cell-free DNA in the recipients' plasma. The data reveal much about the fundamental structure of the human virome in plasma and how it responds to pharmacological perturbation; they also show the relative insensitivity to immunosuppression of the composition of the bacterial component of the microbiome. These data are useful in the design and optimization of post-transplant therapeutic protocols. For example, they show that tapering of antiviral prophylaxis from initial high doses leads to a resurgence of the herpesvirales fraction. CMV DNA load has previously been shown to predict CMV disease relapse and rejection, raising the question of whether patients would benefit from longer-term prophylactic therapy.

The marked expansion in abundance of anelloviridae upon immunosuppression is also worth further consideration. Anelloviruses are ubiquitous in the human population and, although no pathogenicity has been established, anelloviruses are currently under investigation as potential cofactors in carcinogenesis. The sensitivity of anelloviridae to immunosuppression makes organ transplantation an ideal setting for the study of the properties of anelloviridae, particularly in the light of the increased incidence of cancer seen in transplant recipients. The observation of a lower-than-average burden of anelloviruses in patients that suffer from a rejection episode is indicative of insufficient immunosuppression in this subgroup of patients, even though these patients were subject to the immunosuppressant levels prescribed per protocol. This suggests that there would be value in designing assays that allow directly gauging the level of a patient's immunocompetence, in addition to measurements of circulating drug levels. The total burden of anelloviruses identified in a transplant recipient's blood may serve as one such marker of the overall state of immunosuppression of the individual patient.

High throughput DNA sequencing finds use in the hypothesis-free diagnosis of infections. This approach is of particular relevance in the context of transplantation given the fact that infections occur frequently in transplantation and are difficult to diagnose in immunocompromised individuals, and given that sequence analysis can additionally provide information on the graft health through the quantification of donor-derived human DNA circulating in plasma. In other areas of infectious disease, it may be of value to develop subtractive methods to eliminate the human DNA and enrich for DNA of viral and microbial origin.

Experimental Procedures

Clinical sample collection: Patients were enrolled at Stanford University Hospital (SUH) or Lucile Packard Children's Hospital (LPCH), and were excluded if they were recipients of multiorgan transplants. This study was approved by the Stanford University Institutional Review Board (protocol #17666) and enrollment commenced in March 2010. For details on patient recruitment and post transplant treatment of the patients see the extended experimental procedures section.

Plasma processing and DNA extraction: Plasma was extracted from whole blood samples within three hours of sample collection, as previously described (Fan et al., 2008), and stored at −80° C. When required for analysis, plasma samples were thawed and circulating DNA was immediately extracted from 0.5-1 ml plasma using the QIAamp Circulating Nucleic Acid Kit (Qiagen).

Sequencing library preparation and sequencing: Sequencing libraries were prepared from the purified patient plasma DNA using the NEBNext DNA Library Prep Master Mix Set for Illumina with standard Illumina indexed adapters (purchased from IDT), or using a microfluidics-based automated library preparation platform (Mondrian ST, Ovation SP Ultralow library system). Libraries were characterized using the Agilent 2100 Bioanalyzer (High sensitivity DNA kit) and quantified by qPCR. Samples were part of 26 different sequencing runs and were sequenced over the course of 22 months. On average 6 samples were sequenced per lane.

Posttransplant Monitoring and Clinical Sample Collection. This analysis represents a substudy of a prospective cohort study funded by the National Institutes of Health (RC4 AI092673) to study the clinical utility of a donor-derived cell-free DNA assay for the diagnosis of acute and chronic rejection and allograft failure after thoracic organ transplantation. Patients were enrolled if they received a heart or lung transplant at Stanford University Hospital (SUH) or Lucile Packard Children's Hospital (LPCH), and were excluded if they were recipients of multiorgan transplants or if they were followed at centers other than SUH or LPCH posttransplant. This study was approved by the Stanford University Institutional Review Board (protocol #17666) and enrollment commenced in March 2010.

Details of the Posttransplant Therapeutic Protocol, Adult Heart Transplant Recipients. Posttransplant immunosuppression consisted of methylprednisolone 500 mg administered immediately postoperatively followed by 125 mg every 8 hr for three doses. Antithymocyte globulin (rATG) 1 mg/kg was administered on postoperative days 1, 2, and 3. Maintenance immunosuppression consisted of prednisone 20 mg twice daily starting on postoperative day 1 and tapered to <0.1 mg/kg/day by the $6_{th}$ postoperative month and tapered further if endomyocardial biopsies showed no evidence of cellular rejection. Tacrolimus was started on postoperative day 1 and dosing was further adjusted to maintain a level of 10-15 ng/ml during months 0-6, 7-10 ng/ml during months 6-12, and 5-10 ng/ml thereafter. Mycophenolatemofetil was started at 1,000 mg twice daily on postoperative day 1 and dose adjustments were made, if required, in response to leukopenia.

All patients received standard CMV (antiviral) prophylaxis consisting of ganciclovir 5 mg/kg IV, adjusted for renal function, every 12 hr starting on postoperative day 1 unless both donor and recipient were CMV negative. When able to tolerate oral medications, recipients were started on valganciclovir 900 mg twice daily for 2 weeks, then 900 mg daily until 6 months posttransplant, followed by 450 mg daily until 12 months posttransplant, at which point antiviral prophylaxis was discontinued. Valganciclovir dose reductions were made in the setting of leukopenia. CMV-recipients of a CMV+ allograft also received CMV hyperimmune globulin, 150 mg/kg IV, within 72 hr of transplant, 100 mg/kg at posttransplant weeks 2, 4, 6, and 8, and 50 mg/kg at weeks 12 and 16 posttransplant.

CMV⁻ recipients of CMV⁻ allografts were not treated with antiviral prophylaxis until May 2012; subsequently, these recipients were treated with acyclovir 400 mg twice daily for one year. Antifungal prophylaxis consisted of itraconazole 300 mg daily for the first 3 months posttransplant, and prophylaxis against pneumocystis jiroveci infection consisted of trimethoprim/sulfamethoxazole, 80 mg TMP component daily. Prophylaxis against pneumocystis infection was continued indefinitely, and patients intolerant of TMP-SMX were treated with atovaquone, dapsone, or inhaled pentamidine.

All heart transplant recipients were monitored for acute cellular rejection by surveillance endomyocardial biopsies performed at scheduled intervals after transplant: weekly during the first month, biweekly until the $3_{rd}$ month, monthly until the $6_{th}$ month, and then at months 9, 12, 16, 20, and 24. Biopsies were graded according to the ISHLT 2004 revised grading scale (0, 1R, 2R, 3R) (29). Blood samples were collected from heart transplant recipients at the following time points posttransplant: weeks 2, 4, and 6; months 2, 2.5, 3, 4, 5, 6, 8, 10, 12, 16, 20, and 24. A subset of heart transplant recipients also had blood samples collected on posttransplant day 1. If blood sampling and endomyocardial biopsies were performed on the same day, care was taken to ensure that blood was collected prior to the biopsy procedure.

Pediatric Heart Transplant Recipients. Induction immunosuppression initially consisted of daclizumab 1 mg/kg IV every 2 weeks for a total of 5 doses, and was switched to basiliximab 10-20 mg IV on postoperative days 0 and 4 beginning in August 2011. Recipients were also treated immediately with pulse methylprednisolone 10 mg/kg IV every 8 hr for 3 doses, followed by prednisone 0.5 mg/kg twice daily for the first 14 days posttransplant; corticosteroids were subsequently tapered off during the first posttransplant year, in the absence of acute rejection.

Calcineurin inhibition consisted primarily of cyclosporine, with goal levels of 300-350 ng/ml for months 0-3, 275-325 ng/ml for months 4-6, 250-300 ng/ml months 7-12, and 200-250 after month 12 posttransplant. Patients intolerant of cyclosporine were treated with tacrolimus. Protocols for prophylaxis against opportunistic infections and surveillance endomyocardial biopsies were similar to adult heart transplant recipients.

Lung Transplant Recipients. Posttransplant immunosuppression consisted of methylprednisolone 500-1000 mg administered immediately postoperatively followed by 0.5 mg/kg IV twice daily. Basiliximab, 20 mg IV on days 0 and 4, was given for induction immunosuppression. Maintenance immunosuppression consisted of methylprednisolone 0.5 mg/kg IV twice daily on postoperative days 0-3, followed by prednisone 0.5 mg/kg daily until day 30, and subsequently tapered every 2-3 months to 0.1 mg/kg daily during months 6-12 posttransplant. Tacrolimus was started on postoperative day 0 and dosing was adjusted to maintain a level of 12-15 ng/ml during months 0-6, 10-15 ng/ml during months 6-12, and 5-10 ng/ml thereafter. Mycophenolatemofetil was initiated at 500 mg twice daily on postoperative day 0 and dose adjustments were made, if required, in response to leukopenia. Antiviral, antifungal, and PCP prophylaxis were similar to the adult heart transplant cohort.

All lung transplant recipients were monitored for acute cellular rejection by protocol transbronchial biopsies performed at months 1.5, 3, 6, 12, 18, and 24 posttransplant. Biopsies were also performed if indicated for clinical reasons, based on symptoms or pulmonary function test results. Blood samples were collected from lung transplant recipients for study purposes at the following intervals: thrice on day 1, twice on day 2, and once on day 3 posttransplant, followed by weeks 1 and 2, and months 1.5, 2, 3, 4.5, 6, 9, 12, 18, and 24. Blood samples were drawn prior to performance of per-protocol and clinically-indicated biopsies.

Workflow for the Identification of Pathogen-Derived Sequences. Exact duplicates were removed using the C-based utility fastq.cpp. Low-quality reads were removed using the quality filter that is part of the fastx package (fastq_quality_filter-Q33-q21-p50). The remaining reads were subsequently aligned using BWA to the human reference genome build hg19 (bwaaln-q25). Unmapped reads were collected using samtools (samtools view-f4) and low-complexity reads were removed using Seqclean (seqclean-I 40-c1). Reads were subsequently aligned to a selection of viral, bacterial and fungal reference genomes and all references in ncbi_fungi downloaded.

FIG. 6A shows the distribution of the genome sizes. The following parameters were used for the BLAST alignment: reward=1, penalty=_3, word_size=12, gapopen=5, gapextend=2, e-value=10.4, perc_identity=90, culling_limit=2. Blast hits with alignment length shorter than 45 were removed. For a subset of samples longer reads were available (2 3 100 bp, n=55). To test the robustness of the genomic abundance estimates, the length dependence of the composition measurement was examined. Here, reads were trimmed to 40, 50, 65, 80 and 100 bp lengths (fastx_trimmer) and analyzed using the above-described workflow. Here the blast hits with alignment lengths shorter than 37, 45, 59, 72, and 80 bp were removed for the 40, 50, 65, 80 and 100 bp reads respectively. Genome Abundance Estimation Relative genome abundance estimation was calculated with GRAMMy. This tool utilizes the BLAST-derived nucleic acid sequence-similarity data to perform a maximum likelihood estimation of the relative abundance of species in the sample. GRAMMy filters hits by BLAST alignment metrics (E-score, alignment length and identity rate) and accounts for the target genome size and the ambiguity of read assignments in assessing the relative abundance of the candidate reference genomes. Grammy was called using following parameters: python grammy_rdt.py; python grammy_pre.py-q "40,40,1" input set; python grammy_em.py-b 5-t 0.0001-n 100 input.mtx; grammy_post.py input.est set-input.btp.

Custom scripts were used to combine the strain-level abundance estimates to obtain the abundance at higher taxonomic-level abundances. Here, a minimal taxonomy for the reference database was built using Taxtastic.

Quantification Absolute Viral Load. To quantify the load of infectious agents in the samples the blast hit results were collected and the best hits selected for each read using a custom script (Bioperl). FIG. 6B shows the distribution of the number of unique viral, bacterial and fungal blast hits per million unique molecules sequenced. FIG. 6C shows the number of viral, bacterial and fungal genome copies relative to the number of human genome copies present in the sample. The coverage of the genome of the infectious agent was normalized with respect to the human genome coverage.

qPCR Validation of Sequencing Results for Selected Viral Targets. Standard qPCR kits for the quantification of Human Herpes Virus 4, 5 and 6 and parvovirus (PrimerDesign, genesig) were used to validate the sequencing results for a subset of cell-free DNA samples. qPCR assays were run on cfDNA extracted from 1 ml of plasma and eluted in a 100 ml Tris buffer (50 mM [pH 8.1-8.2]). The plasma extraction and PCR experiments were performed in different facilities. No-template controls were ran to verify that the PCR reagents were included in every experiment. FIG. 6D compares the relative number of blast hits per million reads acquired to the concentration of viral genome copies as determined using qPCR.

No-Template Control. A no-template control experiment was performed. A sequencing library was generated from nuclease-free water (S01001, Nugen). The library was prepared together with 7 additional sample libraries (cell-free human DNA) to test for possible sample-to-sample crosstalk during library preparation. To ensure formation of clusters with sufficient density on the Illumina flow cell, the sample was sequenced together with a sample unrelated to the study. Whereas the sample unrelated to the study recruited 16 million reads, the no-template control library generated just 15 reads that mapped to two species in the reference database, the methanocalcodoccus janaschii (9 hits) and *Bacillus subtillis* (5 hits) genomes. No evidence was found for human related sequences, indicating that sample-to-sample contamination was low.

Example 2

Clinical Monitoring of the Virome

Figure 10:
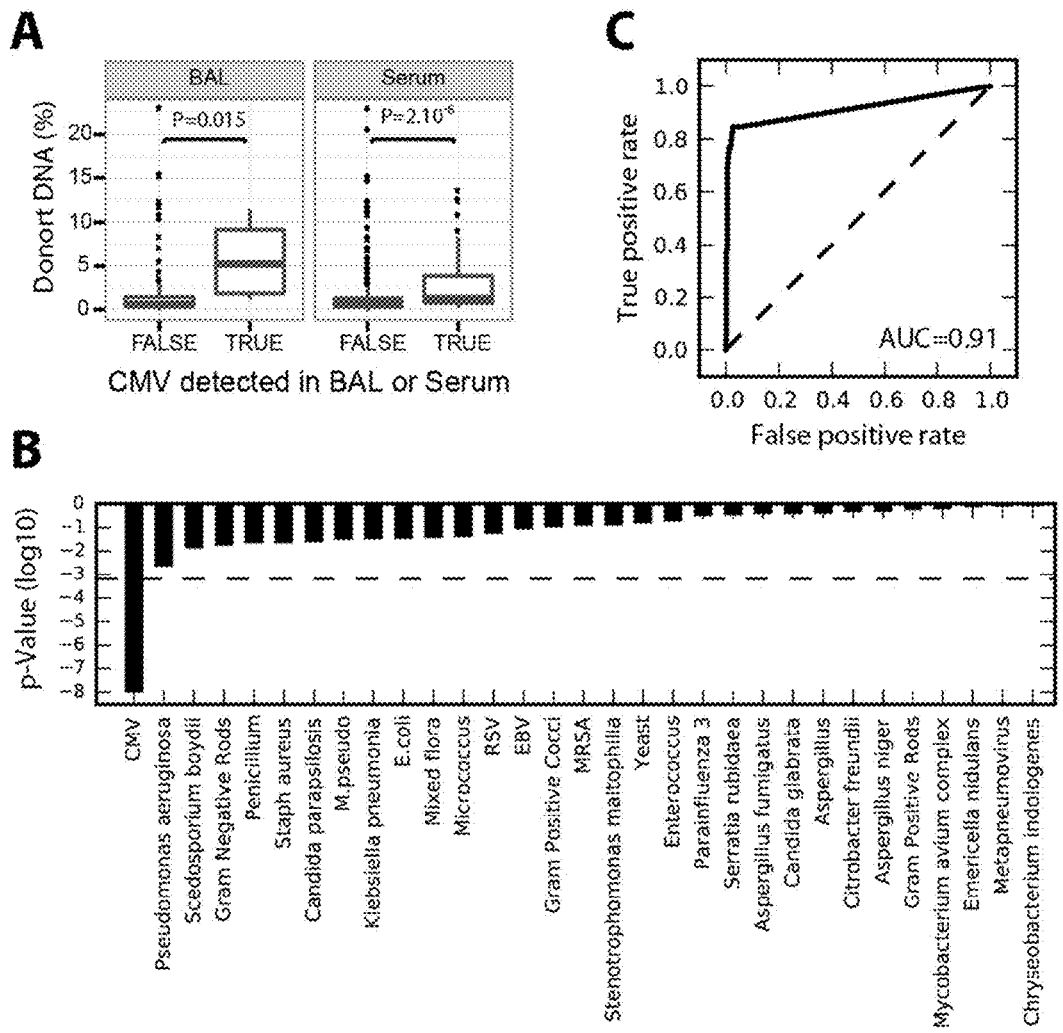
FIG. 10. CMV-infection induced allograft injury. A. Correlation between clinical report of CMV (Human herpes virus 5, HHV-5) infection from specific body fluids (BAL and serum) with donor organ cfdDNA signal matched to clinical test date (P-values; Mann-Whitney U test). B. P-values for the correlation between clinical diagnosis of infection and cell-free DNA level (dashed line indicates the bonferonni-corrected significance threshold) for infections with greater than one clinical positive test result. C. An ROC curve that tests the performance of CMV derived cell-free DNA level in CMV-positive and CMV-negative patients (AUC=0.91).

Using the methods as described in Example, 1 reads that map to the CMV genome were quantified for each sample. An increased CMV abundance was observed in samples that were clinically positive for infection ($p=7.10^{-9}$, Mann-Whitney U test, FIG. 10C); the level of CMV-derived DNA in our samples matched clinical reports of CMV with an AUC of 0.91 (FIG. 10C). This data indicates that CMV surveillance can be performed in parallel with rejection monitoring using the same sequence data, and led us to examine whether other viral infections could be similarly monitored.

Figure 11:
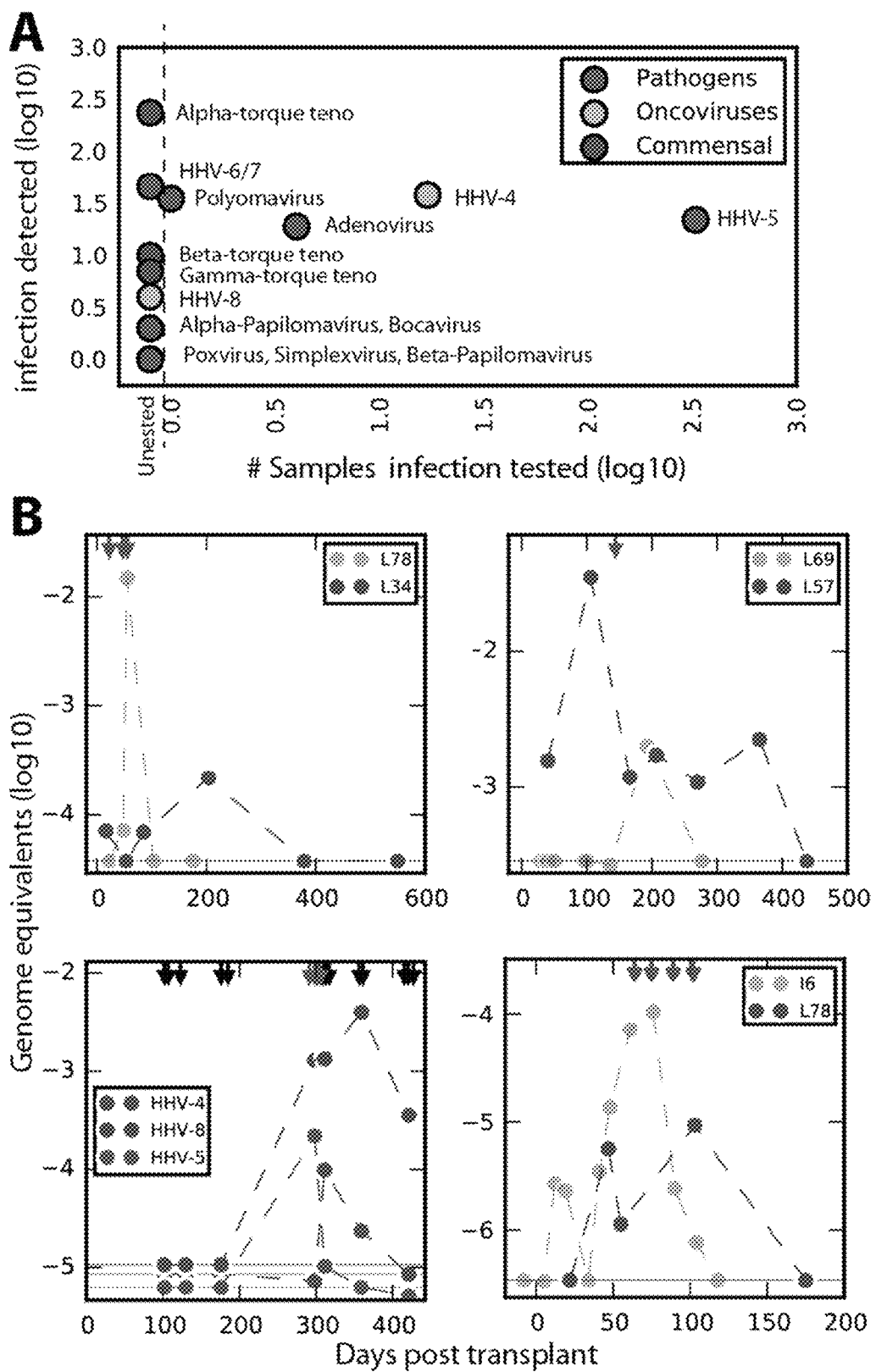
FIG. 11. Monitoring the infectome. A. Clinical testing frequency compared to the incidence of viral infections detected in sequencing. B. Time-series data for patients who tested positive (red arrows) for specific infections relative to those who were un-tested. (1) Adenovirus signal in L78 with clinical positives highlighted relative to untested patient (L34). (2) Polyomavirus signal in L69 with one positive test relative to sustained signal in un-tested patient (L57). (3) Three herpesvirus infections (HHV-4, 5, and 8) in L58 with both positive (red) and negative (black) tests for CMV (HHV-5) highlighted. (4) Microsporidia signal in 16, with four positive tests shown, relative to the signal observed in L78, which had symptoms of microsporidiosis, but was un-tested. Data are logged genome equivalents relative to human where zero values were replaced with the detection limit of the assay (the number of genome equivalents consistent with a single sequence read assigned to the target genome).

We identified well-characterized pathogenic and oncoviruses (FIG. 11A) as well as commensal torque teno viruses (TTVs, alphatorquevirus genus), which is consistent with previous observations of a link between immunosuppression and TTV abundance. The frequency of clinical testing for these viruses varied considerably, with frequent surveillance of CMV (Human Herpes Virus 5, HHV-5, n=1082 tests in our cohort) relative to other pathogens (FIG. 11A). We evaluated the incidence of infection (number of samples in which a given virus is detected via sequencing) relative to the clinical screening frequency. Although CMV was most frequently screened for (335 samples), its incidence as determined by sequencing (detected in 22 samples) was similar to that of other pathogens that were not routinely screened, including adenovirus and polyomavirus (clinically tested on four occasions and one occasion, respectively, FIG. 11A).

Adenovirus is a community-acquired respiratory infection that can cause graft loss in lung transplant recipients and poses a particularly high risk for paediatric patients. Samples were collected from one paediatric patient (L78, FIG. 11B panel 1) that tested positive for adenovirus. This patient also had the highest adenovirus-derived DNA load across the entire cohort. A sustained adenovirus load was furthermore observed in several other adult transplant patients that were not screened clinically (e.g, L34, FIG. 11B panel 1), as testing is typically restricted to paediatric lung transplant cases.

Polyomavirus is the leading cause of allograft rejection after renal transplantation but is not routinely included in post-lung transplant surveillance. We detected polyomavirus in two patients that were not tested for this pathogen (L57 and L15, FIG. 11B panel 2). In both cases, the clinical records indicated persistent renal insufficiency, which may have resulted from polyomavirus infection.

In a last example of the benefit of broad and hypothesis-free screening of infections, we examined a patient that exhibited a high load of human herpes virus (HHV) 8 (FIG.

11B panel 3), an oncovirus that can cause complications following solid-organ transplantation. This patient (L58) tested positive for two other herpesviruses (HHV-4a and HHV-5), which have the potential to stimulate HHV-8 re-activation. Though post-transplant monitoring for HHV-8 is only recommended in particular clinical circumstances, use of sequencing enables the identification of the virus in non-suspect cases that would otherwise go undetected.

Clinical monitoring of the microbiome. In addition to viruses measured in serum, we also observed correlation between cell-free measurements and fungal or bacterial infections detected in other body fluids, including *Klebsiella Pneumonia* infections detected via urine culture (ROC=0.98) and fungal infection detected in BAL. Performance on bacterial and fungal correlations was sensitive both to the infection type and body fluid queried. We observed better performance for body fluids that have tighter coupling to blood and also observed sensitivity to background signal. For example, the most commonly cultured bacterial infection (*Pseudomonas*) was detected in cell-free measurements for over 80% of our patient samples, which was in stark contrast to the most commonly detected viral pathogenic species (CMV), detected in only 6% of our patient samples.

This highlights an important distinction between commensal infections (including *Pseudomonas*), which are part of the normal flora, and non-commensal infections, which are solely pathogenic and have a lower background signal. This distinction may explain differences in sensitivity and specificity measured for commonly cultured commensal infections (e.g., AUC=0.66 and 0.62 for *P. aeruginosa* and *E. coli*, respectively) relative to non-commensals (AUC=0.91 for CMV). In the case of commensal bacteria, the clinical question is not presence or absence but rather presence or absence in inappropriate body sites.

In our cohort, we also detected cell-free DNA derived from microsporidia, a non-commensal fungus that can cause intestinal infections in immunosuppressed patients. We measured a sustained microsporidia load in L78 (FIG. 11B panel 4), a patient that exhibited canonical symptoms of microsporidiosis. An Adenovirus infection (L78, FIG. 11B panel 1) was the suspected cause, though endoscopy and sigmoidoscopy results were inconclusive and stool samples tested negative for C. diff as well as Adenovirus. Based upon our sequencing data, the microsporidiosis is the most likely explanation for the patient's symptoms, as the microsporidia signal measured in this patient is similar to that of 16, a patient from an unrelated cohort that tested positive for microsporidia (FIG. 11B panel 4).

With more than 10 billion fragments per ml of plasma, circulating cell-free DNA is an information-rich window into human physiology, with rapidly expanding applications in cancer diagnosis and cancer treatment monitoring, genetic prenatal diagnosis, and monitoring of heart transplant rejection via "genome transplant dynamics" (GTD). In this work, we applied the principle of GTD to lung transplantation—a particularly challenging type of solid organ transplant that is limited by poor survival rates, as well as an inaccurate and invasive test for allograft rejection.

Because lung transplant recipients with allograft infection and acute rejection may present clinically with similar symptoms, we extended the scope of GTD to infectious disease monitoring. We first demonstrated a strong correlation between clinical test results and cfDNA derived from CMV—a leading cause of post-transplant graft injury. We further showed that hypothesis-free infection monitoring revealed numerous un-tested pathogens, including un-diagnosed cases of adenovirus, polyomavius, HHV-8, and microsporidia in patients who had similar microbial cfDNA levels compared to patients with positive clinical test results and associated symptoms. These examples illustrate the benefit of broad, sequencing-based monitoring of infection as opposed to pathogen specific testing. The approach can be of immediate use as tool that can assist in determining the occurrence and source of an infection. This may be of particular relevance in the context of transplantation, where the incidence of infections is high, where rejection and infection can co-occur, and where the symptoms of infection and rejection are difficult to discriminate.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of processing a sample from a human subject, the method comprising:
    (a) providing a biological sample selected from the group consisting of plasma, serum, cerebrospinal fluid, and synovial fluid, wherein the biological sample is obtained from a human subject and comprises cell-free nucleic acids, wherein the cell-free nucleic acids comprise microbial cell-free nucleic acids;
    (b) separating cells and their fragments from the cell-free nucleic acids in the biological sample using a process that includes centrifuging the biological sample at a force that is at least 4,500 g to generate a biological cell-free sample;
    (c) performing high-throughput sequencing on the cell-free nucleic acids and generating at least 1,000 sequence reads from the cell-free nucleic acids;
    (d) aligning a portion of the at least 1,000 sequence reads from the cell-free nucleic acids with a plurality of microbial reference sequences to obtain a plurality of alignments; and
    (e) using the plurality of alignments to identify microbial nucleic acids in the biological sample.

2. The method of claim 1, further comprising extracting the cell-free nucleic acids from the biological sample.

3. The method of claim 1, wherein the cell-free nucleic acids comprise cell-free DNA.

4. The method of claim 3, further comprising extracting the cell-free DNA from the biological cell-free sample.

5. The method of claim 1, wherein the cell-free nucleic acids comprise cell-free RNA and further comprising extracting the cell-free RNA from the biological cell-free sample.

6. The method of claim 1, wherein (e) comprises using the plurality of alignments to identify bacterial nucleic acids in the biological sample.

7. The method of claim 1, wherein (e) comprises using the plurality of alignments to identify viral nucleic acids in the biological sample.

8. The method of claim 1, wherein (e) comprises using the plurality of alignments to identify fungal nucleic acids in the biological sample.

9. The method of claim 1, wherein (e) comprises using the plurality of alignments to identify parasite nucleic acids in the biological sample.

10. The method of claim 1, wherein the microbial nucleic acids identified in the biological sample comprise nucleic acids from:
   (i) at least one virus selected from the group consisting of: adenovirus, adeno-associated virus, anellovirus, human cytomegalovirus, human respiratory syncytial virus, human rhinovirus, human influenza virus, human coronavirus, human SARS coronavirus, hepatitis virus, cytomegalovirus, parainfluenza virus, human papillomavirus, Epstein-Barr virus, and human T-lymphotropic virus;
   (ii) at least one bacterium selected from the group consisting of: *Brucella, Treponema, Mycobacterium, Listeria, Helicobacter, Legionella, Streptococcus, Neisseria, Clostridium, Staphylococcus, Pseudomonas, Micrococcus*, Multi-drug resistant *Staphylococcus Aureus* (MRSA), *Klebsiella pneumonia*, gram positive bacteria, gram negative bacteria, and *Bacillus*;
   (iii) at least one parasite selected from the group consisting of: *Trichomonas, Toxoplasma, Giardia, Cryptosporidium, Plasmodium, Leishmania, Trypanosoma, Entamoeba, Schistosoma*, Filariae, Ascaria, and *Fasciola*;
   (iv) at least one fungus selected from the group consisting of: *Candida, Aspergillus*, and yeast; or
   (v) any combination thereof.

11. The method of claim 1, wherein the centrifuging the biological sample at a force that is at least 4,500 g comprises centrifuging the biological sample at force that is at least 10,000 g to generate a biological cell-free sample.

12. The method of claim 1, wherein the centrifuging the biological sample at a force that is at least 4,500 g comprises centrifuging the biological sample at force that is 4,500 g to 20,000 g to generate a biological cell-free sample.

13. The method of claim 1, wherein the biological sample is a plasma sample.

14. The method of claim 1, wherein the biological sample is a plasma sample extracted from whole blood within three hours of collection of the whole blood.

15. The method of claim 1, further comprising attaching adapters to the cell-free nucleic acids.

16. The method of claim 15, further comprising amplifying the cell-free nucleic acids using primers specific for the adapters.

17. The method of claim 1, further comprising amplifying the cell-free nucleic acids.

18. The method of claim 17, wherein the amplifying the cell-free nucleic acids comprises performing non-biased amplification of the cell-free nucleic acids.

19. The method of claim 1, further comprising using the plurality of alignments to identify human sequence reads.

20. The method of claim 19, further comprising removing the human sequence reads when identifying the microbial nucleic acids.

21. The method of claim 1, further comprising using the plurality of alignments to determine a quantity of microbial nucleic acids in the biological sample.

22. The method of claim 21, further comprising using the quantity of microbial nucleic acids in the biological sample to detect infection in the human subject.

23. The method of claim 22, further comprising administering an antimicrobial treatment to the human subject to treat the infection.

24. The method of claim 1, wherein (b) generates at least 10,000,000 sequence reads.

25. The method of claim 1, wherein (b) generates at least 100,000,000 sequence reads.

26. The method of claim 1, further comprising detecting antimicrobial resistance in the microbial nucleic acids based on the sequence reads from the microbial nucleic acids.

27. The method of claim 1, further comprising obtaining a second sample from the subject with an infection at a second time point and performing (b)-(e) on the second sample.

28. The method of claim 27, wherein the second time point is a time point following administration of an antimicrobial treatment to the human subject, and further comprising detecting a decrease in quantity of the microbial nucleic acids in response to the antimicrobial treatment.

29. The method of claim 1, further comprising predicting infection in the human subject based at least in part on using the plurality of alignments to identify microbial nucleic acids in the biological sample.

* * * * *